(12) United States Patent
Bendele et al.

(10) Patent No.: US 9,572,483 B2
(45) Date of Patent: Feb. 21, 2017

(54) COMBINED IRRIGATION AND RINSING TUBE SET

(71) Applicant: Medivators Inc., Minneapolis, MN (US)

(72) Inventors: Travis Henry Bendele, Conroe, TX (US); Christopher Steven Adams, Montgomery, TX (US); Dina Grudo, Allen, TX (US); Don Byrne, Montgomery, TX (US); Leon Russ Smith, Conroe, TX (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 14/318,328

(22) Filed: Jun. 27, 2014

(65) Prior Publication Data

US 2014/0316205 A1 Oct. 23, 2014

Related U.S. Application Data

(63) Continuation of application No. 13/273,032, filed on Oct. 13, 2011, now Pat. No. 8,764,642, which is a (Continued)

(51) Int. Cl.
*A61B 1/12* (2006.01)
*A61B 1/00* (2006.01)
*A61B 1/015* (2006.01)

(52) U.S. Cl.
CPC ........... *A61B 1/126* (2013.01); *A61B 1/00119* (2013.01); *A61B 1/00128* (2013.01); *A61B 1/00137* (2013.01); *A61B 1/015* (2013.01)

(58) Field of Classification Search
USPC .................................................. 600/157–159
See application file for complete search history.

(56) References Cited

U.S. PATENT DOCUMENTS 3,707,241 A * 12/1972 Taylor ............... B65D 41/0414
215/337
3,828,963 A * 8/1974 Moller .................. B65D 53/00
215/337

(Continued)

FOREIGN PATENT DOCUMENTS

GB 786282 11/1955
JP 2004-242877 * 9/2004

(Continued)

OTHER PUBLICATIONS

PCT/US2011/056176, International Search Report and Written Opinion of the International Searching Authority, mailing date Jan. 20, 2012.

(Continued)

*Primary Examiner* — Matthew J Kasztejna
(74) *Attorney, Agent, or Firm* — Sorell, Lenna & Schmidt, LLP; William D. Schmidt, Esq.

(57) ABSTRACT

A combined tube set for a disposable water bottle for a medical instrument includes a cap with threads suitable for attachment to various water bottles. The combined tube set provides a first tube set for rinsing that includes an air and water tubes, and air/water connector The combined tube set also provides a second tube set for irrigation that includes an irrigation connector, backflow valve(s), and flexible tubing section. In some embodiments, the tube set can provide warm and/or humid gas to the endoscope.

23 Claims, 19 Drawing Sheets

Related U.S. Application Data continuation-in-part of application No. 13/164,766, filed on Jun. 20, 2011, which is a continuation-in-part of application No. PCT/US2011/041133, filed on Jun. 20, 2011.

(60) Provisional application No. 61/393,238, filed on Oct. 14, 2010.

(56) References Cited

U.S. PATENT DOCUMENTS

| | | | |
|---|---|---|---|
| 4,114,775 A * | 9/1978 | Shinozaki | B65D 41/0464 206/807 |
| 4,552,130 A * | 11/1985 | Kinoshita | 600/158 |
| 4,997,429 A | 3/1991 | Dickerhoff et al. | |
| 5,381,924 A | 1/1995 | Kiefel | |
| 5,405,323 A | 4/1995 | Rogers et al. | |
| 5,437,654 A | 8/1995 | McVay | |
| 5,470,324 A | 11/1995 | Cook et al. | |
| 5,782,383 A | 7/1998 | Robinson | |
| 6,142,979 A | 11/2000 | McNally et al. | |
| 6,210,322 B1 | 4/2001 | Byrne | |
| 6,264,636 B1 | 7/2001 | Holm et al. | |
| 6,303,347 B1 | 10/2001 | Johnson et al. | |
| 6,390,315 B1 | 5/2002 | Giddings et al. | |
| 6,485,412 B1 | 11/2002 | Byrne | |
| 6,523,711 B1 | 2/2003 | Hughes et al. | |
| 7,066,902 B1 | 6/2006 | Ott et al. | |
| 2002/0092858 A1 | 7/2002 | Bowman | |
| 2003/0029876 A1 | 2/2003 | Giraud | |
| 2003/0073971 A1 | 4/2003 | Saker | |
| 2003/0189023 A1 | 10/2003 | Gonzalez | |
| 2007/0238929 A1 | 10/2007 | Aizenfeld et al. | |
| 2008/0125758 A1 | 5/2008 | Marisi | |
| 2011/0263939 A1 | 10/2011 | Kaye et al. | |
| 2012/0088974 A1 | 4/2012 | Maurice | |

FOREIGN PATENT DOCUMENTS

| | | |
|---|---|---|
| JP | 2006094758 | 4/2006 |
| WO | 2010/028172 A1 | 3/2010 |

OTHER PUBLICATIONS

PCT/US2011/056185, International Search Report and Written Opinion of the International Searching Authority, mailing date Jan. 19, 2012.

Notification of Transmittal of the International Search Report and the Written Opinion of the International Searching Authority, or the Declaration (Oct. 24, 2011).

* cited by examiner

COMBINED IRRIGATION AND RINSING TUBE SET

This application is a continuation application of co-pending U.S. patent application Ser. No. 13/273,032 filed Oct. 13, 2011 and entitled "Combined Irrigation and Rinsing Tube Set", which claims the benefit of the filing date of U.S. Ser. No. 13/164,766 filed Jun. 20, 2011 and PCT Application No. US2011/41133 filed Jun. 20, 2011 and U.S. Provisional Application Ser. No. 61/393,238, filed Oct. 14, 2010. These entire disclosures of these documents are hereby incorporated by reference into the present disclosure.

FIELD

This application relates to medical instrument systems. More particularly, a combined tube set for insufflation, irrigation and rinsing that allows an endoscopic system to be connected to a water bottle.

BACKGROUND

Endoscopic instruments have been developed to provide surgeons with an internal view of the organ or body passage requiring treatment. Such endoscopes typically have channels through which flexible instruments, such as a miniaturized forceps, are inserted and advanced. The endoscope assembly includes an elongated flexible cable equipped at one end with an eyepiece or other viewing means and at the other end with an imaging means. The cable transmits images or image-producing signals from the illuminated operative site to the viewing means so that the surgeon will have visual confirmation of the action of the instrument's working end. The cable also provides a flow passage for the delivery of fluid (liquid or gas) for irrigation, insufflation, rinsing, or other purposes. It may be necessary to provide the optic head with a flow of sterile water. The passage of the sterile water across the optic head prevents the buildup of materials on the imaging means. This flow of water operates, in a sense, like a windshield wiper/washer assembly.

In normal practice, the endoscopic instrument has a control body, which provides several ports that allow connectors to be attached for irrigation, insufflation, rinsing, or other purposes. These ports may include a variety of fittings that are suitable for various purposes. For example, air and water ports can receive an air/water connector suitable for providing air and/or water for rinsing and other purposes. As such, the air and water are delivered through the connector into the light guide connector of the endoscope. The light guide connector or the control body can also include an irrigation port so as to allow irrigation water to be directly provided to the endoscope. Suitable valves are provided on the control body so as to control the flow of water and/or air through the control body and the flexible cable of the endoscope.

Unfortunately, there is usually a great expense associated with maintaining sterility of the equipment and/or water. Sterile water can be provided for rinsing from a water bottle that is connected to the endoscopic instrument via tubing. The tubing has a fitting at one end so as to allow the tube to be connected to the air/water port of the endoscopic instrument, and the other end of the tubing is inserted into the water bottle. Typically, the fitting will include two tubes, one providing water and the other providing air. Sometimes the two tubes may be concentric with an inner tube providing water and an outer tube providing air. The inner tube extends through a cap into the water bottle, and the outer tube is connected to the cap of the water bottle. Air may be delivered through the area between the inner tube and the outer tube so as to pressurize the interior of the water container. In some embodiments, the gas that pressurizes the bottle and insufflates the lumen may be supplied through a separate tube that interfaces with the bottle cap; in such a system, the gas flows from the bottle to the endoscope through the space between the inner tube and the outer tube. The gas flowing into the bottle increases the pressure within the bottle. When a valve in the endoscope is opened, the pressure in the bottle will force water to flow through the inner tube and into the endoscope at a desired rate. For example, inner and outer tube sets that are utilized with endoscopes are described in U.S. Pat. Nos. 6,210,322 and 6,485,412. These entire disclosures are herein incorporated by reference into the present application.

The purpose of irrigation is to clear debris from the field of view. When debris such as digestive waste, mucous, blood, and detached tissue cover portions of the lumen wall, the operator may be unable to make a proper assessment of the condition of the tissue or perform actions such as biopsy removal or cautery. When irrigation is desired, the endoscopic instrument can be connected to another water bottle using another set of tubing. One end of an irrigation tube is connected to an irrigation port of the endoscopic instrument, and the other end of the tubing extends through a cap so that it may be placed in a water bottle. The irrigation tube may provide a section of flexible tubing that is insertable into a peristaltic pump. The peristaltic pump provides water flow to the endoscope that is suitable for irrigation. The irrigation system moves water by drawing it out of the bottle with a peristaltic pump, so it requires a vent to allow air to enter the bottle. In contrast, the insufflation and lens rinsing system moves water by pushing it out of the bottle with internal pressure, so the tubing and bottle assembly must be sealed to maintain the pressure.

After usage, the two water bottles, the tubing, and the associated fittings are sterilized or disinfected if they are not disposable items. In the case that the items are disposable, two water bottles, tubing, and associated fittings are discarded. If the items are sterilized or disinfected, there is a considerable labor expense associated with cleaning, and disinfecting or autoclaving. Additionally, there is also the possibility of residual contaminants residing in the area of connection between the tubes and the bottle. This creates a considerable expense to the hospital in either case. In some systems, two bottles are required when the user desires to perform both functions (irrigation and rinsing) because the designs of these systems treat them as separate and independent, individual systems.

Research has demonstrated that there is a clinical benefit when insufflation is performed using warm (e.g. body temperature) water instead of dry room temperature air. It is expected that this benefit is due to the fact that the warm water is more similar to the natural surroundings of the internal tissue than the cool, dry air. The sudden loss of temperature caused by insertion of air can make the muscles in the lining of the lumen contract and affect blood flow to the tissue. Also, when warm water is used for insufflation, the debris remaining on the tissue is readily washed away, which improves visibility for cancer screening when the user removes the water and adds air for insufflation. Warm water infusion typically is performed as the endoscope is inserted into the patient. The water is subsequently removed and replaced with air as the endoscope is being removed and the operator is looking for problematic tissues (such as cancerous tumors).

Just as the tissue is most commonly subjected to warm liquids and not cool dry air, the gas that does pass through the digestive tract tends to be warm and humid. Thus it is advantageous to use warm, humid gas whenever insufflation is performed with gas. In some endoscopic systems, the gas that enters the endoscope for insufflation first passes through the water bottle and then into the endoscope. In such a system, it is possible to warm the gas prior to it entering the bottle and/or warm the water in the bottle. If the gas is then forced to enter the bottle at the bottom and bubble to the top, it absorbs water and heat then leaves the bottle warm and humid as it travels to the endoscope for insufflation. The luminal wall may cramp if the tissue is dried or cooled by the gas used for insufflation. If the gas used for this procedure is carbon dioxide instead of atmospheric air, the carbon dioxide absorbs into the tissues more than 100 times faster.

The absorption rate of carbon dioxide into digestive tissues is 100 to 150 times that of oxygen and nitrogen, which combine to make up about 99% of atmospheric air. Because carbon dioxide is absorbed into the tissues and expired through the respiratory system, the gas in the lumen does not have to pass through the remainder of the digestive system, thus improving patient comfort and speeding recovery.

The lens rinsing system, similar to the irrigation system, comprises a continuous liquid path interrupted only by valves. (The irrigation system fluid path also is interrupted by the pump rollers.) It is desirable to maintain sterility of the water in the water bottle that serves as a source of water for lens rinsing. Thus, it is desirable to add a check valve in the lens rinsing flow path. This check valve is, in some embodiments, incorporated in the air/water connector of the tube set since the valve can then be disposed of with the tube set rather than being reprocessed with the endoscope. The check valve can help to prevent cross-contamination.

Thus, there is a need to develop new devices and methods to reduce or eliminate the risk of contaminating the tube set used in endoscopic procedures and reduce or eliminate the risk of infecting the patient.

SUMMARY

New devices and methods are provided that reduce or eliminate the risk of contaminating the endoscopic tube set and reduce or eliminate the risk of infecting the patient. In some embodiments, a water bottle adapter is provided for use with an endoscopic instrument. The water bottle adapter includes a cap suitable for attachment to the neck of a water bottle with a first set of tubing for rinsing and a second set of tubing for irrigation. The first set of tubing includes air and water tubes. One end of the first set of tubing provides a first connector that can be attached to a port on an endoscopic instrument. This first connector may have one or more check valves to prevent water, air, and other medical gasses from moving in an undesirable direction. The end of the air tube opposite the connector is connected to the water bottle cap, and the end of the water tube opposite the connector is connected to the water bottle cap and extends through the water bottle cap. The second set of tubing for irrigation may provide for a flexible section of tubing that is insertable into a peristaltic pump. One end of the irrigation tubing provides a second connector that can be attached to an irrigation port of the endoscopic instrument, and the other end extends through the water bottle cap.

In some embodiments, there is a combined tube set comprising: a first tube set utilized to provide rinsing fluid for an endoscope, wherein the first tube set provides an air tube and a water tube; and a second tube set utilized to provide irrigation fluid for the endoscope, wherein the second tube set provides a flexible section.

In some embodiments, there is a combined tube set comprising: a first tube set utilized to provide rinsing fluid for an endoscope, wherein the first tube set provides an air tube and a water tube; a second tube set utilized to provide irrigation fluid for the endoscope, wherein the second tube set provides a flexible section; and a third tube utilized to provide gas to the system.

In some embodiments, there is an adapter that passes water and gas between a tube set with separate gas, irrigation water, and rinsing water tubes and an endoscope.

In some embodiments, there is an adapter that passes water and gas between a tube set with separate gas and rinsing water tubes and an endoscope.

In some embodiments, there is a tube set utilized to provide rinsing fluid to an endoscope, wherein the tube set provides an air tube and a water tube, with a filter in the air path.

In some embodiments, there is a tube set utilized to provide rinsing fluid for an endoscope, wherein the tube set provides an air tube and a water tube, with a backflow check valve in the water path.

In some embodiments, there is a tube assembly comprising: a first tube set configured to provide a liquid to an instrument, wherein the first tube set provides a gas and the liquid to the instrument; and a second tube set configured to provide the liquid to the instrument, wherein the second tube set may comprise a flexible section.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
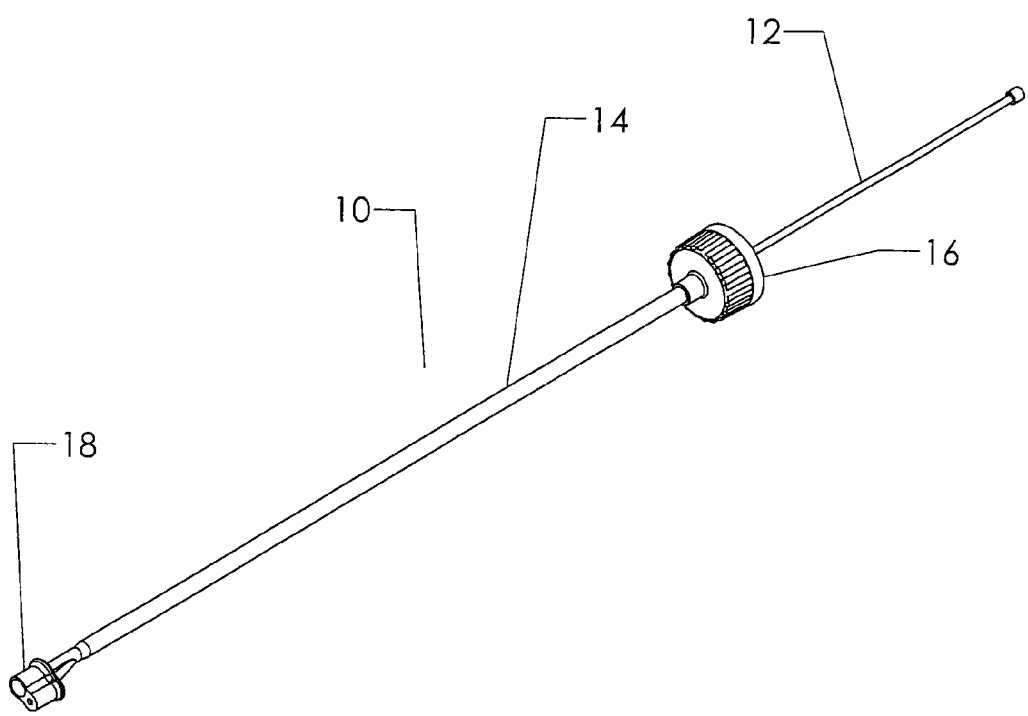
FIG. 1 illustrates an embodiment of an air/water tube set.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

It is noted that, as used in this specification and the appended claims, the singular forms "a," "an," and "the," include plural referents unless expressly and unequivocally limited to one referent. Thus, for example, reference to "a tube set" includes one, two, three or more tubes.

We refer now to the drawings wherein depicted elements are not necessarily shown to scale and wherein like or similar elements are designated by the same reference numeral through the several views.

FIG. 1 shows an example of a system for connecting a water bottle to an endoscope for gas insufflation and lens rinsing or an air/water tube set 10. Tube set 10 includes water tube 12 and air tube 14. While water tube 12 extends through air tube 14 in the example shown, it should be noted that in other embodiments the water and air tubes may be separated or the water tube may not extend through the air tube. Tube set 10 provides a connector 18 on one end of the tube set that can be connected to an endoscope (not shown). Cap 16 is connected to the air tube 14 and water tube 12 extends through cap 16. In some embodiments, the current system is configured to be used with a single bottle. However, it will be understood that, in some embodiments, more than one bottle can be used.

Figure 2:
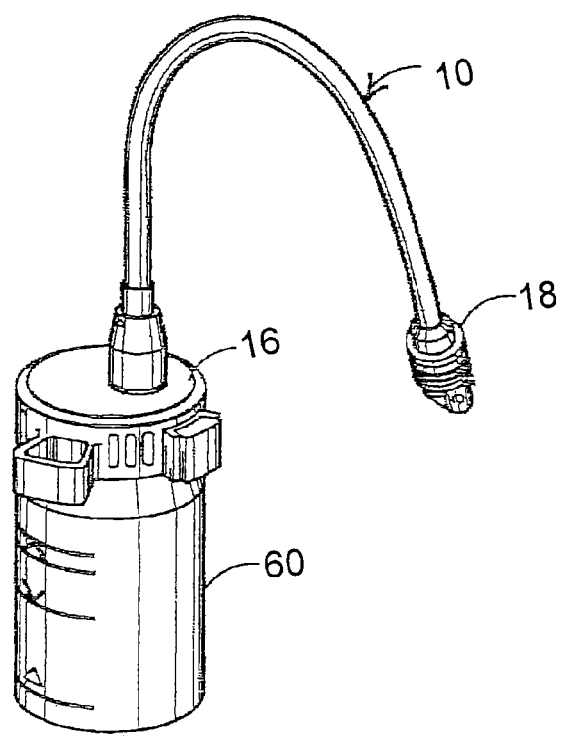
FIG. 2 illustrates an embodiment of an air/water tube set secured to a water bottle.

FIG. 2 shows an example of an air/water tube set 10 attached to water bottle 60. When cap 16 is placed on a water bottle, water tube extends into the water bottle to provide a source of water for the endoscope. Connector 18 (shown as an Olympus connector in contrast to FIG. 1) may be connected to ports on the endoscope to provide water for lens rinsing.

Figure 3:
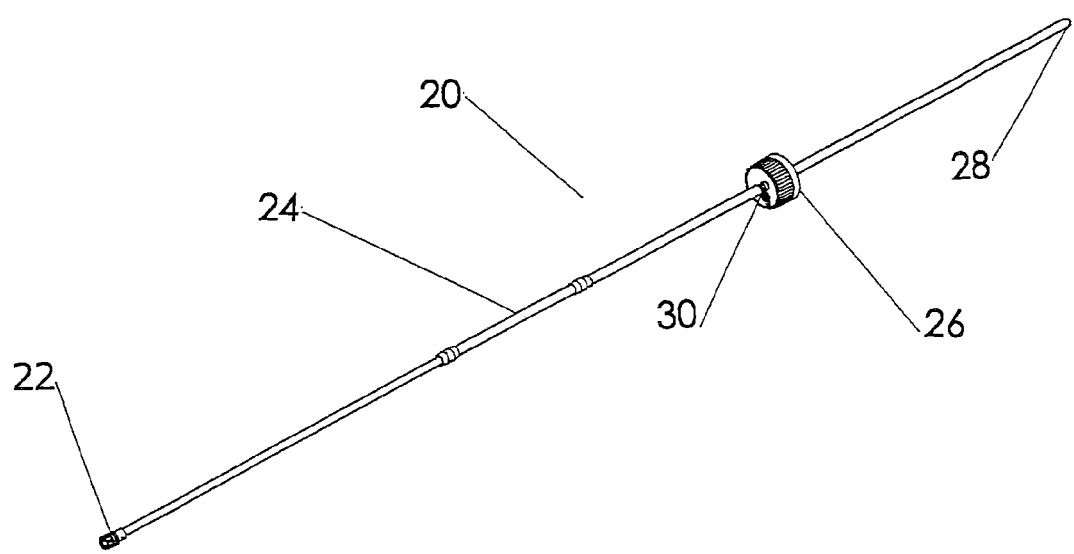
FIG. 3 illustrates an embodiment of an irrigation tube set.

FIG. 3 shows an example of a system for connecting a water bottle to an endoscope for irrigation or an irrigation tube set 20. One end of the irrigation tube set 20 has a connector 22 that can be mated to an endoscope. Irrigation tube set 20 may include flexible section 24 of tubing that can be inserted into a peristaltic pump, which pumps the water to the endoscope for irrigation. Irrigation tube set 20 is attached to cap 26 and the water bottle end 28 of the irrigation tube set 20 passes through the cap so that it may extend into a water bottle when the cap is placed on the water bottle. While the irrigation tube set 20 is formed from three separate pieces of joined tubing as described, in other embodiments, irrigation tube 20 may be formed from fewer or more joined tubes. Cap 26 provides vent 30. Since the pump is drawing water through the tubing, an equivalent volume of air may be allowed to enter the bottle. In the embodiment shown, the air is filtered, whereas in some embodiments the air is not filtered, so it may enter by some other gap in the system.

Figure 4:
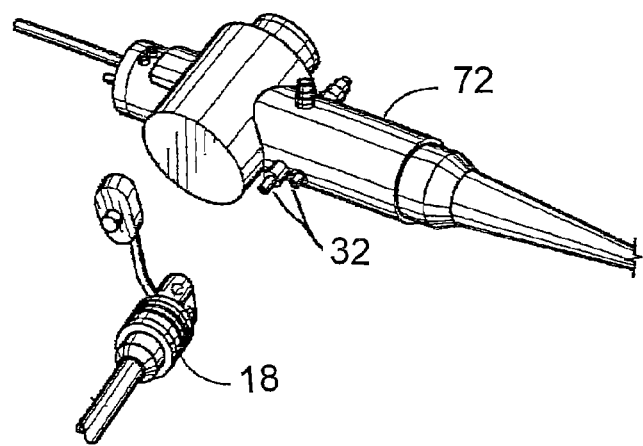
FIG. 4 illustrates an embodiment of an endoscope.

FIG. 4 shows an example of endoscope light guide connector 72 with several ports, such as air/water ports 32 and irrigation port (not shown). Connector 18 for air/water tube set 10 connects to air/water ports 32 of endoscope 72. Connector 22 for irrigation tube set 20 (of FIG. 3) connects to irrigation port (not shown) of endoscope 72. When connectors 18 and 22 (of FIG. 3) are connected to endoscope 72 water for lens rinsing or irrigation can be provided to the endoscope and the gas insufflation system can be pressurized.

Air/water tube set 10 and irrigation tube set 20 require two separate water bottles for use with endoscope 72. If the tube sets and water bottles are reusable, great expense is associated with maintaining sterility of the equipment and/or water. There is a considerable labor expense associated with manual or automated cleaning, and disinfection or autoclaving the equipment. Additionally, there is also the possibility of residual contaminants remaining in the area of connection between the tubes and the bottle. Further, because air/water tube set 10 and irrigation tube set 20 each require their own water bottle more equipment must be sterilized, or disposed of if not reusable, after the equipment has been used.

Additionally various types of water bottles and water containers exist for endoscope systems. Presently, disposable water bottles are manufactured in 250 milliliter, 500 milliliter and 1,000 milliliter sizes. These water bottles have slightly varying diameter necks of slightly varying lengths. The thread structure on the neck of each of these water bottles is slightly different. The difference in the length of neck and configuration of threads is the result of water bottles being manufactured by several different companies utilizing their respective designs. As such, a need has developed so as to allow for the adaptation of the various water containers to the various endoscope systems, which are offered. Any standardization that can be achieved will eliminate the need to maintain an inventory of products for each of the various types of water bottles available. Although an endoscope is shown in FIG. 4, it will be understood that other medical instruments can be used with the present tube assembly and/or cap. These instruments include, for example, colonoscopes, laparoscopes, bronchoscopes, or any medical instruments with a camera that requires use of fluid (e.g., water, saline solution, dextrose solution, Ringers solution, Lactated Ringer's solution, or combinations thereof or the like) for use.

Figure 5A:
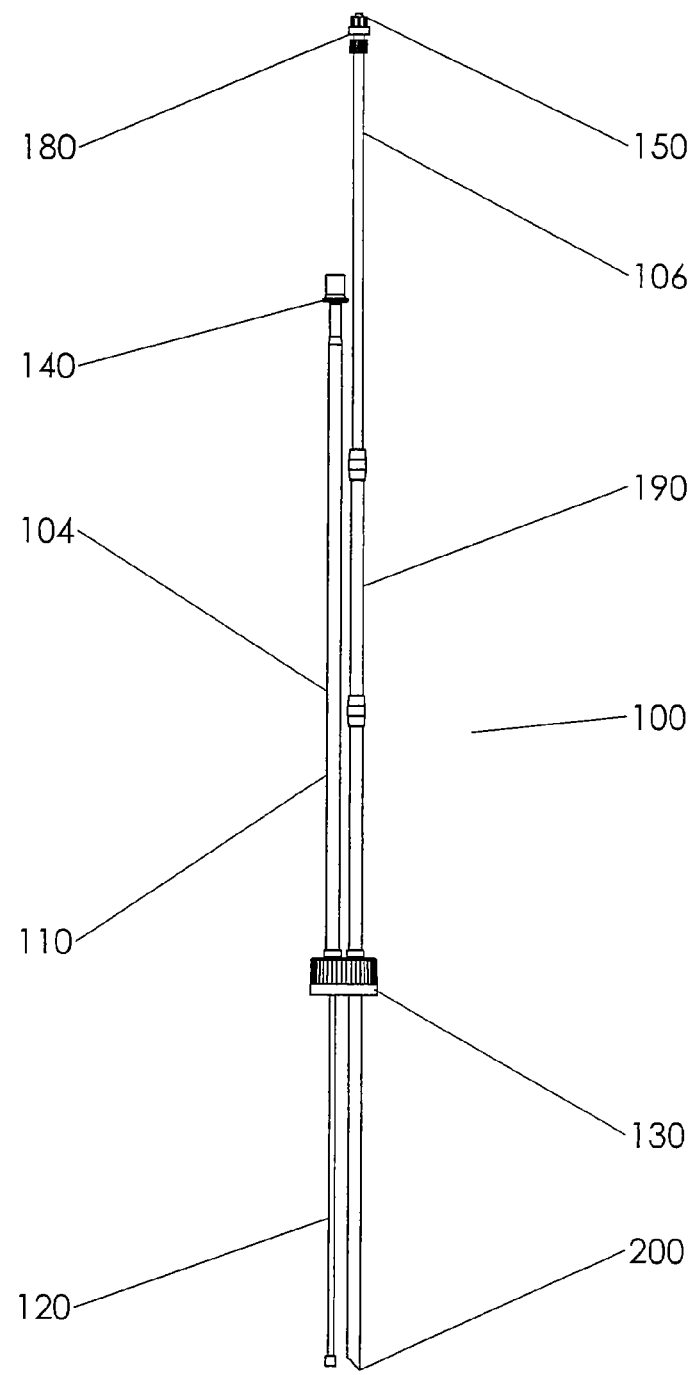
FIG. 5A illustrates an embodiment of a combined irrigation and air/water tube set.

FIG. 5A shows an illustrative embodiment of a combined tube set 100. Combined tube set 100 includes air/water set 104, irrigation tube set 106, bottle cap 130, air/water connector 140, and irrigation connector 150. Irrigation connector 150 can be a universally adaptable connector, such as a luer connector. Irrigation connector 150 can alternately be a connector designed for direct connection to the endoscope. The air/water tube set 104 is shown as a water tube 120 extending through air tube 110 from bottle cap 130 to air/water connector 140. While air/water connector 140 is shown as a connector suitable for connection to an Olympus® endoscope, it should be recognized that any suitable connector may be utilized to facilitate the various types and/or brands of endoscopes used during the endoscopic procedure.

Air/water connector 140 and/or irrigation connector 150 can alternately be a universally adaptable connector design. Further, in other embodiments, the tubing arrangement of the tube sets may also be modified to accommodate various types and/or brands of endoscopes. For example, the air/water connector 140 and the irrigation connector 150 may utilize any variety of connector that is suitable for connecting combined tube set 100 to any type or brand of endoscope or a fitting may be mated with an adapter body that allows a tube set to be utilized with a particular brand and type of endoscope (e.g. U.S. Pat. Nos. 6,210,322 and 6,485,412). In some embodiments, a universal connector or adapter connected to the endoscope may receive both air/water connector 140 and the irrigation connector 150. For example, combined tube set 100 may be suitable for connection with a Fujinon® AJ-510 or Byrne Medical 100141 adapter. Further, in some embodiments, the universal connector may be moved away from the endoscope as shown in FIG. 5C. While water tube 120 extends through air tube 110 in the embodiment shown, in some embodiments, the air tube and water tube may be separated i.e. the water tube is not contained within the air tube. In a separated air and water tube arrangement, air/water connector 140 may provide a fitting that may be mated with an adapter body that provides a connector that is suitable for connection with an endoscope utilizing a concentric air and water tube arrangement.

In the air/water tube set 104, water tube 120 extends from air/water connector 140 through the bottle cap 130. Air tube 110 has a larger diameter than water tube 120 and extends from air/water connector 140 to bottle cap 130. Air tube 110 and water tube 120 may be made from a plastic material, elastomeric material, or any suitable material or combination of materials. Air tube 110 and water tube 120 may be secured to air/water connector 140 by ultraviolet gluing, any suitable adhesive, or any suitable attachment means. While water tube 120 passes through bottle cap 130, air tube 110 may be secured to bottle cap 130 by ultraviolet gluing, any suitable adhesive, or any suitable attachment means. Because air tube 110 has a larger diameter than water tube 120, an annular air passage is created between the outer surface of water tube 120 and the inner surface of air tube 110. The annular air passage extends from bottle cap 130 to air/water connector 140.

Bottle cap 130 can be secured to the neck of a water bottle (not shown), thereby allowing an end of water tube 120 to extend into the water bottle. Bottle cap 130 can be made of a plastic material, elastomeric material, and/or any suitable material or combination of materials. Water tube 120 may have an anchor 160 attached to one end to weigh down water tube 120 into the liquid contained in the water bottle. Weight 160 serves to assures that end of water tube 120 will reside adjacent to the bottom of the sterile water bottle. Weight 160 provides an opening (not shown) that allows fluid to pass through water tube 120 to air/water connector 140. In some embodiments, weight 160 may be omitted. Weight 160 can be ultravioletly glued to end of water tube 120 or secured by any suitable adhesive or any suitable attachment means.

Bottle cap 130 has inner threads which are particularly adapted for joining with the threads of a variety of different water bottles, as discussed in more detail below. Bottle cap 130 may include one or more gaskets (not shown) to facilitate a substantially air tight seal between bottle cap 130 and a water bottle. When bottle cap 130 is secured to a water bottle and air/water connector 140 is connected to an endoscope, air may pass from the endoscope to the water bottle via the annular air passage created between the outer surface of water tube 120 and the inner surface of air tube 110. Note that in other embodiments the tubes may be separate. Because bottle cap 130 creates an air tight or nearly air tight seal, forcing air into the water bottle creates pressure in the bottle that forces water through a first end of water tube 120 having weight or anchor 160 towards a second end of water tube 120 having air/water connector 140. Although a weight or anchor 160 is shown, this is an optional component and the tube set does not require a weight or anchor.

Irrigation tube set 106 is also connected to bottle cap 130 to provide combined tube set 100. Irrigation tube set 106 includes irrigation connector 150, back flow valve(s) 180, and flexible tubing section 190. A first end of irrigation tube set 106 provides irrigation connector 150, which may be connected to an endoscope. In contrast to air/water tube set 104, irrigation tube set 106 provides a single tube. Irrigation tube set 106 may be made from a plastic material, elastomeric material, or any suitable material or combination of materials.

Irrigation tube set 106 may include one or more backflow valves 180 to prevent backflow of water into the water bottle. Irrigation tube set 106 may include flexible tubing section 190, which is insertable into a peristaltic pump. In the embodiment shown, backflow valves 180 is placed at the end of tube set 106 that connects to the endoscope. However, in other embodiments, one or more backflow valves 180 may be placed elsewhere on irrigation tube set 106, such as near tube end 200 which is placed in the water. Backflow valves 180 prevent or limit backflow of water back into the water bottle, thereby reducing the risk of potential contamination of the sterile water. In some embodiments, backflow valves may also be utilized in the air/water tube set 104. The backflow valve can be different designs, for example, a flap valve, duck-bill valve or the like.

Tubes of the irrigation tube set 106 may be secured to bottle cap 130, irrigation connector 150, and/or backflow valve(s) 180 by ultraviolet gluing, any suitable adhesive, or any suitable attachment means. When bottle cap 130 is placed on a water bottle, water source end 200 of irrigation tube set 106 extends into the water bottle. As with water tube 120 of air/water tube set 104, water source end 200 of irrigation tube set 106 may include an anchor or weight (not shown) to weigh down water source end 200 towards the bottom of the sterile water bottle.

Separated tube sets shown in FIGS. 1 and 3 include two separate water bottles that may not be fully utilized during the use of an endoscope. When the use of the endoscope is complete, the two water bottles may be discarded to prevent future contamination of the water and/or equipment. Further, if the tube sets are disposable, two tube sets are discarded. If the tube sets are reusable, the equipment must be manually or automatically cleaned and disinfected or autoclaved to sterilize the equipment for future use. In contrast, combined tube set 100 allows a water source for irrigation and rinsing to be provided by a single water bottle used during the endoscopic procedure, thereby minimizing waste. Further, combined tube set may be made of a low cost, disposable material so that labor and cost associated with cleaning and autoclaving is avoided.

Figure 5B:
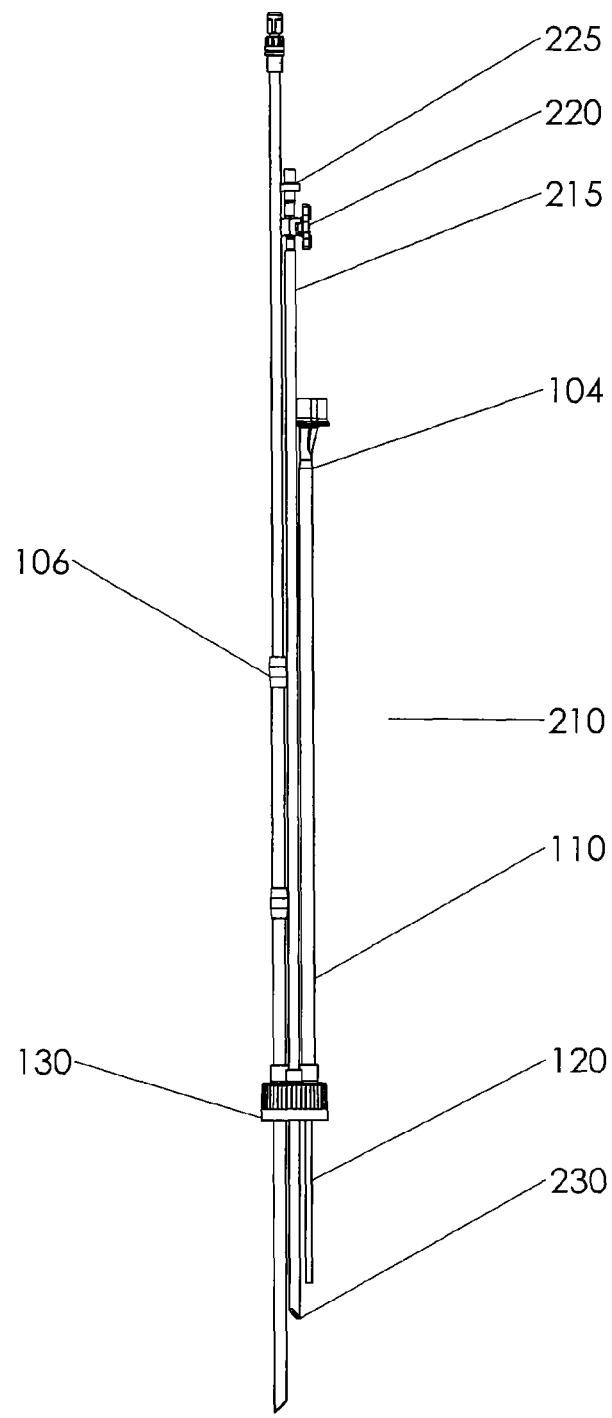
FIG. 5B illustrates an embodiment of a combined irrigation, air/water, and gas tube set.
Figure 5C:
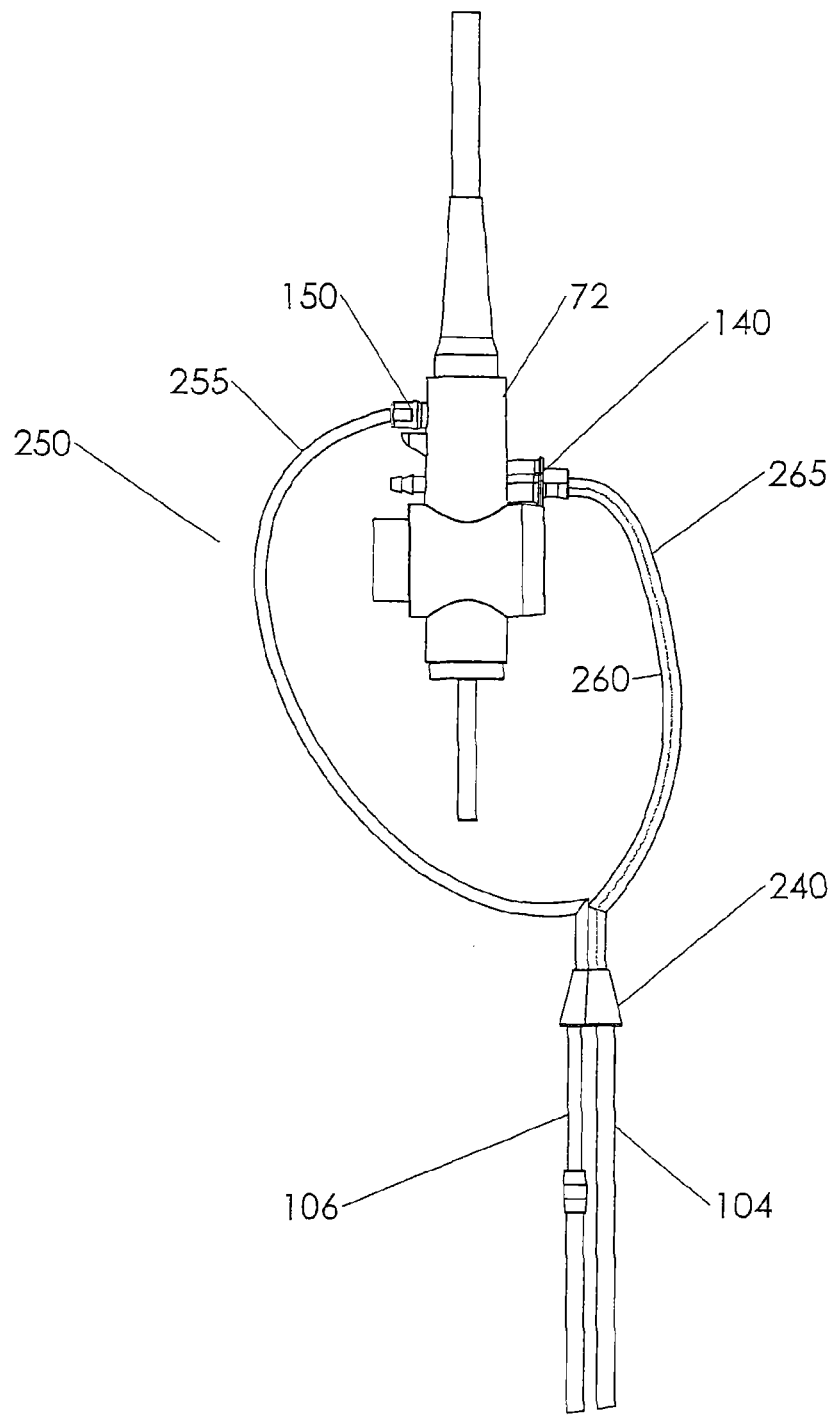
FIG. 5C illustrates an embodiment of a universal connector for a combined irrigation and air/water tube set.

FIG. 5B is an illustrative embodiment of a tube assembly (e.g., combined irrigation, air/water, and gas tube set) 210. Combined irrigation, air/water, and gas tube set 210 may provide an air/water tube set 104, irrigation tube set 106, and bottle cap 130 similar to the tube set shown in FIG. 5A. Additionally, combined irrigation, air/water, and gas tube set 210 also provides gas tube set 215. Gas (e.g. air, carbon dioxide, nitrogen, oxygen, or combination thereof or other medical gas) may be supplied to the bottle by gas tube set 215 attached to bottle cap 130. Gas supply connector 225 may be connected to a gas source and gas valve 220 may be utilized to open and close the flow of gas into a water bottle. Gas valve 220 is optional and may not be utilized in other embodiments. Gas supply connector 225 may incorporate a backflow valve, which allows gas to flow in only one direction. In some embodiments, the backflow valve may be located at end 230 of gas tube set 215. When gas valve 220 is open, gas flows into the bottle through the gas tube set 215, pressurizes the bottle, and passes from the bottle cap 130 to the endoscope via the annular passage created between the outer surface of water tube 120 and the inner surface of air tube 110. End 230 of gas tube set 215 extends through bottle cap 130, to the bottom of the water bottle. As a result, gas entering the container bubbles up through the water and is humidified. When the gas is preheated and/or the water is preheated, the result is a warm, humid gas that is then passed to the endoscope and then to the patient for insufflation. While end 230 of gas tube set 215 extends through bottle cap 130 in the embodiment shown, in other embodiments end 230 may stop at bottle cap 130. In an embodiment where end 230 of tube set 215 does not extend into the water, the gas passed to the patient may be pre-humidified or dry gas may be delivered to the patient.

In some embodiments, the present application is designed to be used with warm gas, such as for example, carbon dioxide which is provided to gas tube set 215 by a carbon dioxide gas source, such as for example a tank, which is then humidified as it is bubbled through the liquid (e.g., water) in the bottle. In some embodiments, the bottle (e.g., 60 in FIG. 2) can be heated by for example an external heating source (e.g., hot plate, microwave, etc.). In this way the gas and/or liquid in the bottle can be heated.

In some embodiments, the gas can be humidified by passing the gas in the direction of the cap 130 in the opposite direction of water flow to the fluid in the bottle. In some embodiments, the gas may be pressurized and fed into the tube under pressure.

The gas is humidified by bubbling it through the fluid and pressurizes the bottle, and passes from the bottle cap 130 to the endoscope via the annular passage created between the outer surface of water tube 120 and the inner surface of air tube 110. End 230 of gas tube set 215 extends through bottle cap 130, to the bottom of the water bottle. In some embodiments, the end of the tube 230 can have a tip configured to decrease bubble size (e.g., the diameter and/or surface area of the tip can be reduced) to increase the rate of humidification as the smaller bubbles will increase the humidification rate of the gas. In some embodiments, the tip of the gas tube can be angled to increase the orifice size so that the gas exiting it has decreased surface area. The gas will pressurize the bottle and the humidified gas will pass through inner surface of air tube 110 and to adapter 103 next to air/water tube 104 to the endoscope.

In some embodiments, the air/water tube 104 has outer surface of water tube 120 running within inner surface of air tube 110 creating an annular passage between the outer surface of water tube 120 and the inner surface of air tube 110 to allow air and fluid out of the tube to the adapter 103 to air/water tube 104 to the endoscope. It will be understood that the combined air/water tube can be a tube within a tube structure as shown in FIG. 5B or two separate tubes that do not have a tube within a tube structure (not shown). In some embodiments, the outer surface of the water tube 120 runs continuously or discontinuously within the air tube 110. In the embodiment shown in FIG. 5B, the water tube protrudes from the cap 130 into the bottle, but the air tube does not run into the bottle. The water tube 120 is discontinuous with the air tube 110. In some embodiments, the cap 130 may further comprise rims 131 that protrude from the cap and guide the tubes. It will be understood that the cap 130 can have none, one, two, three, four, five or more rims that guide the tubes out of the cap. In some embodiments, the cap 130 can have one, two, three, four, five or more channels that allow the one or more tubes to pass through them. In FIG. 5B, there are three channels that allow the tube to pass through it, but there is still an air tight seal so only air and liquid can pass out of the bottle through the tube assembly. In some embodiments, and as shown in FIG. 5B, the irrigation tube has flexible section or portion 107 that is more flexible than the rest of the irrigation tube 106. The flexible section or portion 107 is configured to be connected to a pump that allows pumping of the irrigation fluid to the endoscope which can be connected at connector 226. It will be understood that in some embodiments, the irrigation tube, air/water tube and/or the gas tube can have one or more flexible sections, where the tube is more flexible than other sections. It will also be understood that in some embodiments, the irrigation tube, air/water tube and/or the gas tube can have one or more filters, vents, check valves, pinch clips, adapters, and/or connectors disposed above the bottle cap 130. In some embodiments, the air/water tube 104 can have a pinch clip disposed above the bottle cap 130 to stop flow of the gas and/or liquid in the tube. It will be understood that the adapter or connector can be configured to be a permanent part of the tubing, and therefore, not removable without damaging the tubing or it can be configured to be removed from the tubing without damaging the tubing (e.g., a twist and pull fitting, push fitting, pull fitting, twist-off fitting, Luer lock, or the like). In some embodiments, the cap can be vented or not have a vent.

FIG. 5C illustrates an embodiment of a universal connector or adapter 250 for a combined irrigation and air/water tube set attached to an endoscope 72. The air/water tube set 104 and the irrigation tube set 106 bring gas and/or fluid (e.g., water, saline, dextrose, etc.) to the adapter. Air tube 265 and water tube 260 are shown as separate tubes. These tubes can also be combined into one as concentric tubes (not shown). The air tube 265 and water tube 260 run into their respective ports of the air/water connector 140 and, therefore, air and/or water can be drawn into the tubes as required by the user of the endoscope. Irrigation tube 255 can connect to the auxiliary water connector 150, which will allow irrigation fluid to be drawn to the auxiliary water connector 150 and then to the endoscope as needed.

In some embodiments, the adapter can be removably attached to the plurality of tubes, for example, by a fitting or permanently attached to the plurality of tubes. In some embodiments, the adapter comprises a universal adapter that comprises a portion of a plurality of tubes and connectors that can attach to other adapters, connectors, tubes, and/or any endoscope. The user connects the tube set having irrigation tube set 106, air/water tube set 104 to the adapter input connector 240 (the lower portion of these tubes shown below adapter input connector 240). The adapter input connector 240 can then be attached to air tube 265, water tube 260 and irrigation tube 255 (the upper portions of these tubes shown above adapter input connector 240). Each of these tubes have their own connectors (auxiliary water connector 150) (air/water connector 140) configured to be attached to endoscope 72. In this way, the adapter 250 can be a universal adapter and have tubing and connectors designed for a specific endoscope and the user merely connects the adapter to the tube set (below 240) by connecting the tubes into the adapter input connector 240. Therefore, the tube set can be customized to the specific endoscope being used. In some embodiments, the adapter allows connection to a variety of different endoscopes. In some embodiments, the universal connector is compatible with a tube set, and the tube set is compatible with a variety of adapters that are compatible with a variety of endoscopes. In some embodiments, it will be understood that the adapter 240 can be permanently attached to the plurality of tubes and not be detachable.

In some embodiments, there is a tube assembly comprising: a first tube set configured to provide a liquid and a gas to an instrument 72, the first tube set comprising a first tube 265 configured to provide air to the instrument and a second tube 260 configured to provide liquid to the instrument; a second tube set comprising a second tube 255 configured to provide the liquid to the instrument and a bottle cap contacting at least the first tube set and the second tube set.

In some embodiments, there is a tube assembly comprising: a first tube set configured to provide a liquid and a gas to an instrument 72, the first tube set comprising a first tube 265 configured to provide air to the instrument and a second tube 260 configured to provide liquid to the instrument; a second tube set comprising a second tube 255 configured to provide a second liquid to the instrument and a bottle cap contacting at least the first tube set and the second tube set, wherein the second tube set comprises a flexible section configured to be connected to a pump; and a third tube set comprising a third tube configured to provide gas to the instrument. In some embodiments, there will be a first liquid in one tube and a second liquid in another tube. The first and second liquid can be the same type of liquid (e.g., water as the first and second liquid) or the first and second liquid can be a different type of liquid (e.g., water as the first liquid and saline as the second liquid). Therefore, in some embodiments, the irrigation fluid and rinsing fluid can be the same type of fluid (e.g., water, saline, or dextrose, etc.) from the same bottle. It will be understood that the tube assembly, in some embodiments, can be used with a single bottle or multiple water bottles. Alternatively, the bottle can have one, two, three, four or more compartments that contact the tube set, each compartment can have the same fluid in it in all the compartments or a different fluid in each compartment from the single bottle.

Optionally the first tube runs in an interior of a bottle and at least the third tube runs in the interior of the bottle, and the first tube set, second tube set and third tube set run out of a bottle cap, each of the first tube set, second tube set and third tube set comprise at least one of an adapter, a connector, a valve, a filter, pinch clip, or a vent.

In some embodiments, when gas (e.g., carbon dioxide gas) enters through the gas input (e.g., third tube set) tube set and the end of the gas input tube set is extended into the liquid (e.g., water), there is a risk of liquid intake tubes taking in the gas bubbles instead of liquid. This may happen if the entrance to a liquid (e.g., water) intake tube is located next to the gas input tube's outlet or if the entrance to a liquid intake tube is located above the gas input tube's outlet. In the latter case, the bubbles may rise to the end of the liquid intake tube. When a liquid intake tube takes in the gas bubbles, the gas is fed to the medical instrument (e.g., endoscope) instead of a steady stream of liquid. The result is a less effective lens rinsing or irrigation effect.

Therefore, in some embodiments, a gas input tube whose length under the bottle cap is shorter than the length of one or more of the other liquid intake tubes is provided. In some embodiments, one or more tubes in the tube set can be the same or different lengths.

In some embodiments, in addition to the lengths of the tubes being the same or different, there is a separating member (e.g., bracket, clip, hook, loop, prong, channel, spacer, or other separator, or the like) that contacts one or more tubes and separates the gas input tube from any liquid intake tube. The separating member may force a horizontal separation and/or vertical separation between one or more tubes. In some embodiments, the separating member may force a vertical separation so that the gas bubbles are introduced to the liquid at a level higher than that of the liquid intake. In some embodiments, one or more tubes of the device are preformed into some predetermined shape so that the gas bubbles are directed away from the liquid intake tubes. In an embodiment in which the tube sets are constructed from a common, multi-lumen tube, the gas input lumen can be plugged and a hole in the tube wall would be cut for the gas to exit the tube at a higher level.

In some embodiments, the first, second, third and/or fourth tube can be concentric with each other. Therefore, the present application contemplates four tubes combined into one, three tubes combined into one, two tubes combined into one for delivery of liquid and/or gas to a medical instrument. In some embodiments, the present application contemplates using single, double, triple and/or quadruple lumen tubes for delivery of liquid and/or gas to a medical instrument.

In some embodiments, the cap comprises a liner for an air-tight seal. In some embodiments, the length of the first, second, and third tube set is longer in length than the portion of the tube set contained within the bottle.

Figure 6A:
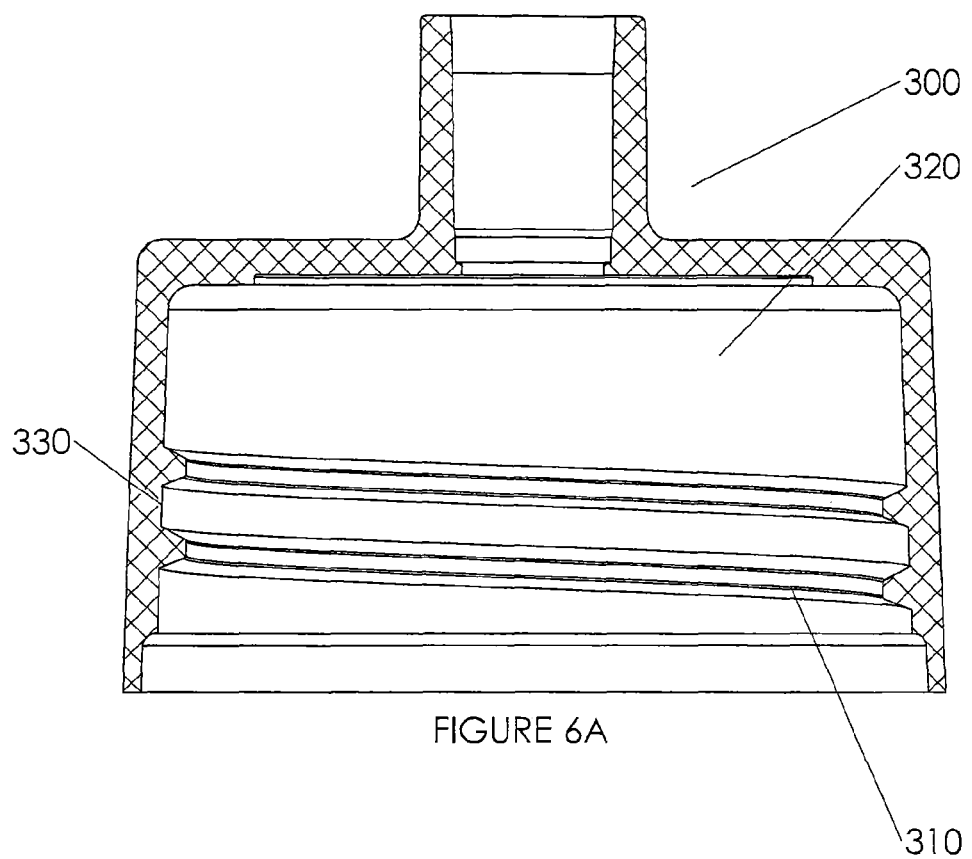
FIG. 6A illustrates an embodiment of a universal fit bottle cap.
Figure 6B:
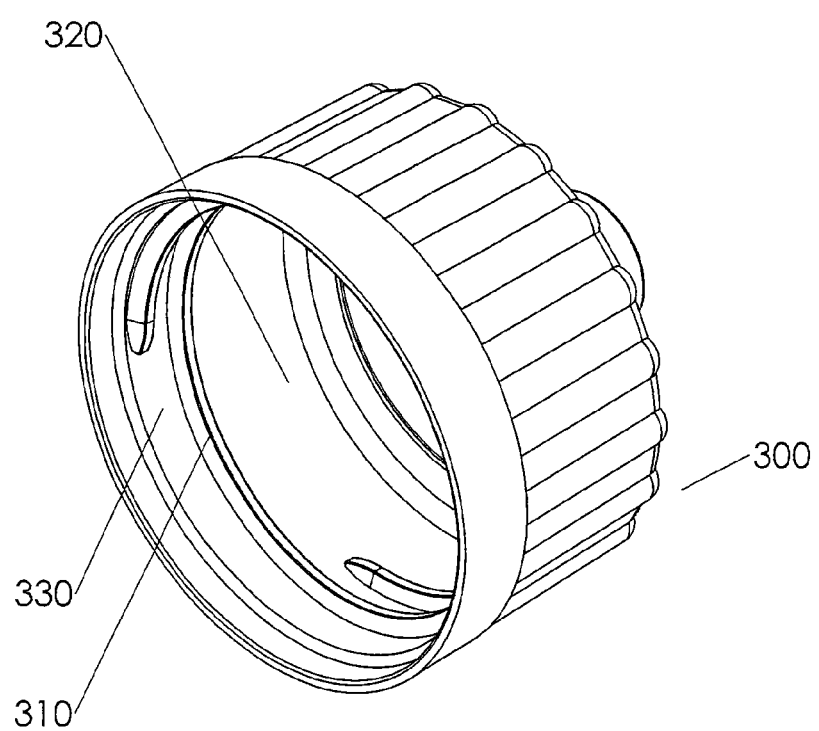
FIG. 6B illustrates an embodiment of an isometric view of a universal fit bottle cap.

FIG. 6A is an illustrative embodiment of a universal fit bottle cap 300, and FIG. 6B is an isometric view of an illustrative embodiment of a universal fit bottle cap 300. Bottle cap 300 may optionally utilize a liner or seal (not shown) to create an air tight seal with a water bottle. Thread(s) 310 on the inner surface of universal fit bottle cap 300 have specific cross-sectional geometry and thread pitch that allow the cap to be utilized with a variety of water bottles. The material from which the cap is made has specific structural and tribological properties (including Young's modulus and coefficient of friction). The dimensions, geometry and pitch of the threads, and material properties of universal fit bottle cap 300 allow it to mate to any of several commercially available water bottles even though the designs of these water bottles vary.

Similarly, the liner material has certain structural and tribological properties (including durometer and coefficient of friction). The liner also has a certain cross-sectional profile. The combined effect of the liner's profile and material properties allow it to form an air tight seal between the bottle cap and any of several different water bottles. Specifically, the inner surface of the liner is shaped so as to continuously contact the bottle around its full circumference, thus sealing the system. If the system is not sealed, it will not function properly. Given that different bottles have rims or ridges of different diameters and at different heights relative to their threads, the liner has a varying inner diameter designed to accommodate each bottle design by contacting it at the appropriate height and diameter. The liner may, if desirable, use gaps, including air gap 301, along the surface contacting the cap in order to allow the liner to conform to the bottle rim. The liner may be formed separately and inserted into the bottle cap. Alternately, the liner may be formed directly into the bottle cap, such as by the process of over molding. Alternately, the bottle cap and the liner may be formed as one contiguous body. Additionally, the liner may also be used to form an air-tight seal between the bottle cap and the aforementioned tube sets.

The bottle cap is preferably made from a rigid polymer such as acrylonitrile butadiene styrene (ABS), polyvinyl chloride (PVC), polystyrene, or polycarbonate. In the embodiment shown, thread 310 has a pitch of 0.160", and thread 310 may travel through a certain number of revolutions. Creating too many revolutions will limit the bottle geometry with which the bottle cap can mate. However, creating too few revolutions can prevent the cap from making a reliable connection to the water bottle. In the embodiment shown, thread 310 travels 1.75 revolutions. The inner diameter of universal fit bottle cap 300 above and below the threads 310 should preferably be wide enough to allow the top of the bottle to pass into region 320 above threads 310. If the inner diameter of universal fit bottle cap 300 is too narrow, it will not be able to travel as far onto the bottle as needed in order to engage the liner for an air-tight seal.

Thread 310 should have a cross section which is thicker at the base (where it meets the wall of the bottle cap) and thinner at the inner surface (nearest the bottle neck). This geometry would resemble a trapezoid. In the present embodiment, the innermost surface should have a thickness of about 0.035" and the thickest portion (near the wall) should have a thickness of about 0.090".

The thread has a minor diameter, measured as the distance across the thread at its surface that extends farthest from the wall of the bottle cap. The thread has a major diameter, measured as the distance across the thread at its base where it joins the wall of the bottle cap. In one embodiment of the universal fit bottle cap 300, threads 310 have a minor diameter of about 1.375" and a major diameter of about 1.490". In another embodiment of the universal fit bottle cap 300, threads 310 have a minor diameter of 1.300" and a major diameter of about 1.420". Surface 330 on which the threads are formed (the inner cylindrical surface of the bottle cap) is tapered at an angle of about 2 degrees so that its diameter is slightly larger at the opening of the cap than at the opposite end of that surface. In order to ensure smooth movement of universal fit bottle cap 300 as it is threaded onto the bottle, threads 310 may not have blunt edges and corners in some embodiments. The corners of the trapezoidal geometry at either end of the 0.035" wide inner surface may be rounded with a fillet whose radius is about 0.005". The two ends of threads 310 may taper in a ramp-like fashion to provide a smooth transition from the thread's minor diameter to it minor diameter.

Figure 6C:
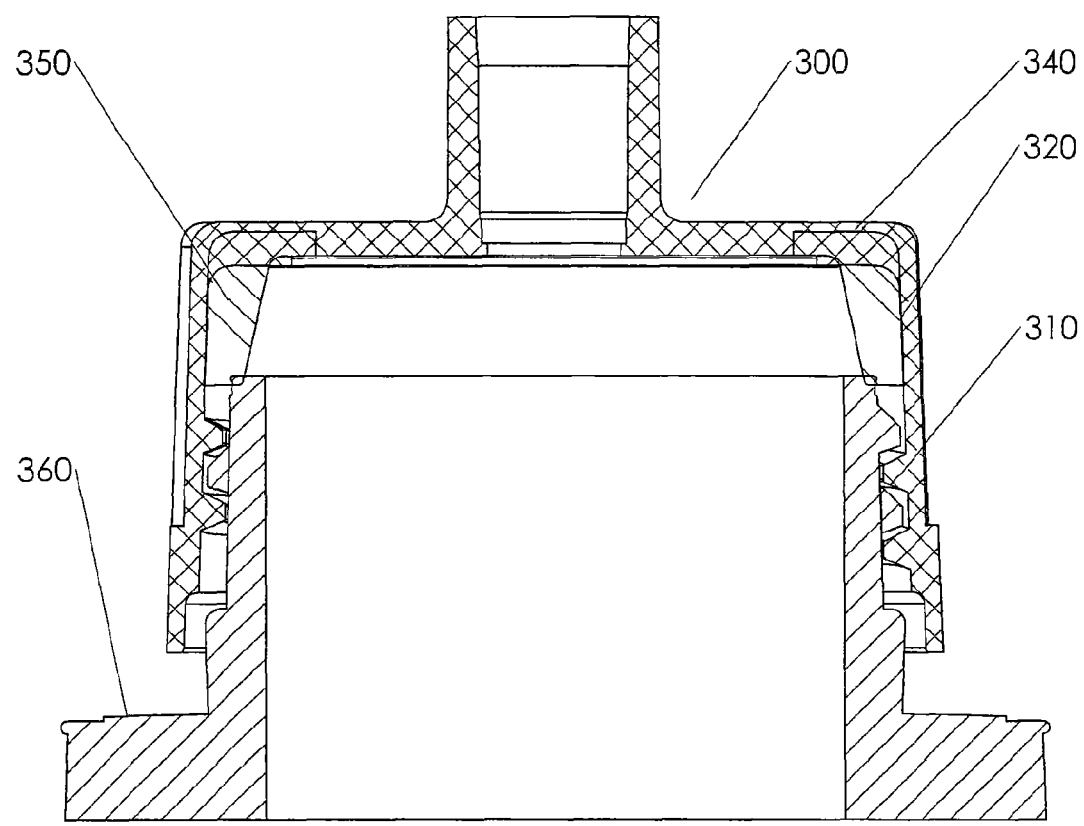
FIG. 6C illustrates an embodiment of universal fit bottle cap threaded on a bottle.

FIG. 6C is an illustrative embodiment of universal fit bottle cap 300 threaded on a bottle. Liner 350 resides in region between threads 310 and top end 340 of universal fit bottle cap 300. Liner 350 engages bottle 360 when universal fit bottle cap 300 is threaded a sufficient distance on to the neck of a bottle and passes 320. Bottles from different manufacturers vary significantly in (1) distance from the bottle thread to the top rim, (2) distance from the bottle thread to the bottle neck's largest outer diameter; (3) the diameter of the bottle's rim; and (4) the bottle neck's largest diameter. The liner is designed to mate to one or both of the largest neck diameter and the top rim for the various bottle geometries. Thus, the liner has an inner surface with an inner diameter that varies over its length. The liner's varying inner diameters and their positions relative to the bottle cap threads cause the liner to engage the bottle neck or rim sufficiently to form an air-tight seal.

In order to maintain pressure within the system to deliver gas for insufflation and water for rinsing the lens, the system must be reasonably air tight. The seal between the bottle and the bottle cap may be maintained by a liner which is a flexible member of the bottle cap assembly. This liner maintains contact with the cap and the bottle by deforming as it is squeezed between the rigid materials of the cap and the bottle. Of particular importance is the geometry of the liner surfaces that are intended to maintain contact with the bottle and cap. A single liner design will be able to maintain an air-tight seal between multiple cap designs and multiple bottle designs. However, in some embodiments, multiple liners may be utilized. In other embodiments, the cap and liner may be integrated into a one piece member such that the cap is a flexible member which forms a seal with the bottle, including bottles of differing geometry.

The bottle cap and the bottle neck have mating threads. As the cap is threaded onto the bottle neck, the liner engages the bottle neck or the bottle throat and forms the seal. Since bottle thread geometries vary, a cap and liner design may engage sufficiently with a variety of bottle geometries sufficiently to hold the cap in place, thus compressing the liner to form a seal with the bottle.

Figure 6D:
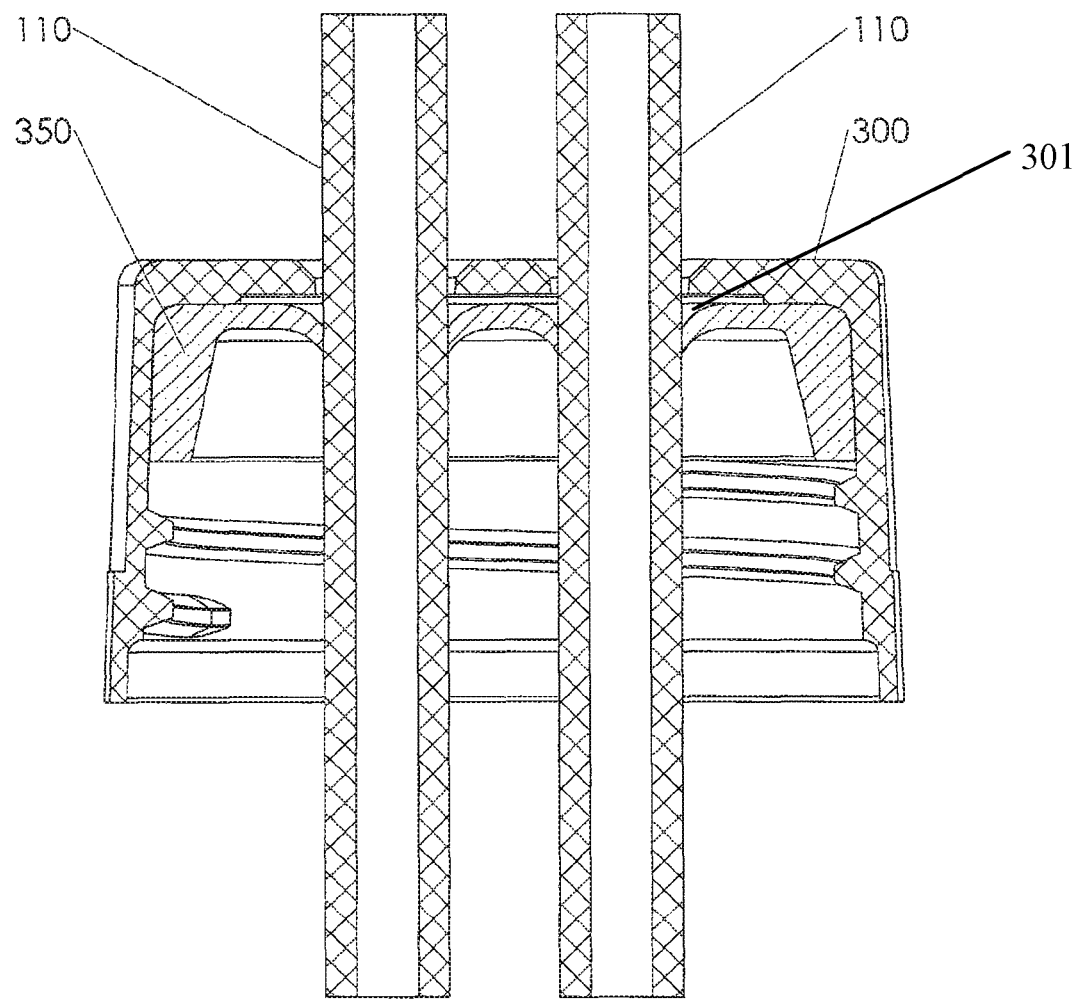
FIG. 6D illustrates an embodiment of a bottle cap and liner.

FIG. 6D is an illustrative embodiment of a bottle cap 300 and liner 350. Another point at which the system must be sealed is between the cap 300 and the tubes 110 connected to the bottle. This also includes the bond between the cap and any other tubes that pass through it necessitating a seal to maintain system pressure. In some cases, the tube may be bonded to the cap with an adhesive bond, a solvent bond, or a mechanical lock such as a swaged fitting. However, in other embodiments, the structural connection between the tube and the cap can make use of a flexible liner so that no adhesive or solvent bond between the tube and cap is needed. This liner may occupy the space between the cap and the tube so that the liner is compressed and thus forms an air-tight seal.

Alternatively, the liner may surround the tube in the region above or below the bottle cap, forming a seal by constricting the tube. Given the proper geometry, the liner's seal against the tube's outer surface may increase its constriction as the pressure within the system increases, forcing the flexible liner material against the outer wall of the tube.

Figure 7:
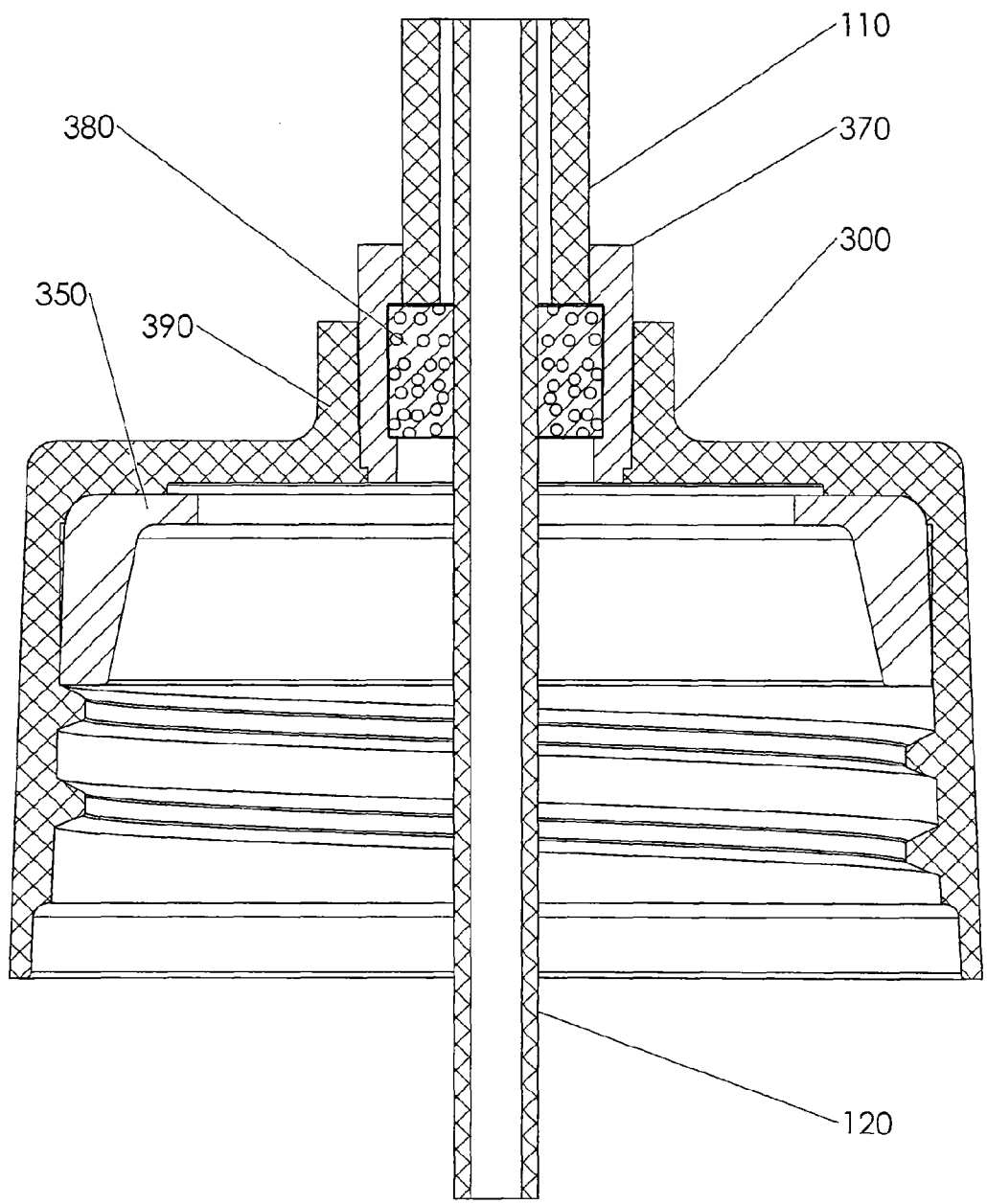
FIG. 7 illustrates an embodiment of air filter incorporated into a bottle cap.

FIG. 7 is an illustrative embodiment of air filter incorporated into a bottle cap. Air tube 110 stops in filter housing 370. Filter housing 370 fits into a nipple 390 of the bottle cap. Water tube 120 passes through the filter medium 380. Water tube 120 and filter medium 380 may be in contact to properly seal the air passageway.

As water is removed from a water bottle, air must be allowed to flow into the bottle. In some embodiments, air may enter the bottle through a filter (microbial, HEPA, etc.) so as to maintain the sterility of the air and water in the bottle. The irrigation system preferably includes a backflow valve or check valve to ensure that contaminated fluid from the patient does not enter the irrigation system e.g., unidirectional flow from the bottle to the endoscope and not in the reverse direction. The irrigation tube that feeds water to the endoscope is typically used on multiple patients in the course of a day, so contamination from a patient that enters the tubing may be passed to subsequent patients. Thus, in some embodiments, a check valve is desirable for maintaining the sterility of the water in the bottle and in the tube set.

In certain procedures, such as ERCP (endoscopic retrograde cholangiopancreatography), extra precaution should be taken to prevent contamination of the patient's anatomy. In such procedures, it is especially desirable to have the protection of a backflow valve (410 In FIG. 8) in the water path and an air filter (500 FIG. 9A) in the air path. The connector that contains the backflow valve and air filter may permanently attach to the tubing of the tube set. Such an embodiment would require a user to replace the entire tube set if the user is concerned about contaminants from the endoscope reaching the tube set's connector. In order to reduce waste and cost, another embodiment features a connector that is removably attached to the tube set. Thus, the portion of the connector that has contacted the endoscope can be discarded, and the tubing, which remains sterile, can receive a new connector with backflow valve and air filter. A backflow valve within the connector can prevent contamination from reaching the tube set. If the connector is removed from the tube set and replaced with a new, sterile connector, the tube set will remain sterile. Thus, when the tube set with the new connector is attached to the next endoscope, which is used on the next patient, the next patient is protected from infection. While it is highly unlikely that the original air/water connector will become contaminated, the ability to replace the connector improves the health care provider's ability to protect the patient.

Figure 8:
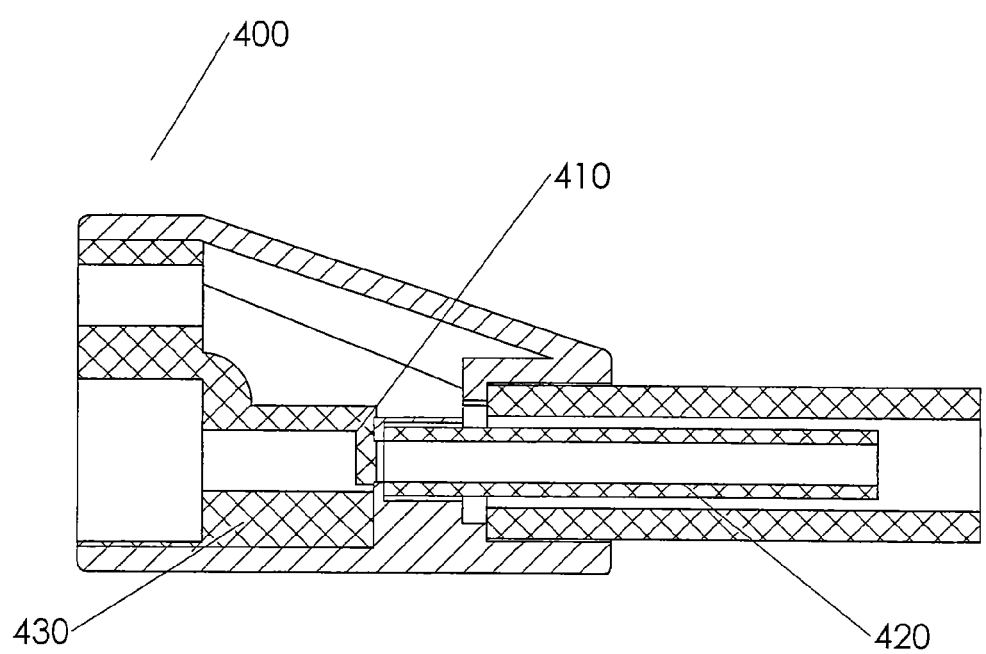
FIG. 8 illustrates an embodiment of an air/water connector with a check valve.

FIG. 8 is an illustrative embodiment of an air and water connector 400 with a check valve. The connector employs a movable flap 410 in the water flow path to prevent water from flowing from the endoscope into the water tube 420.

The flap may be formed from a soft, flexible material such as a thermoplastic elastomer. The flap may be formed from the same body that forms a seal around the water intake tube of the endoscope air/water receptacle. When the pressure in the water tube of the tube set is higher than that in the endoscope's water intake tube (e.g., when the bottle is pressurized and the endoscope's lens rinsing water valve is opened), water will flow from the tube set into the endoscope, forcing the moveable flap open. When there is no pressure differential, the flap comes to rest, preferably in a position that closes or nearly closes the flow path. When the pressure in the water tube of the tube set is lower than that in the endoscope's water intake tube (e.g., when the endoscope's lens rinsing water valve is opened and the pressure in the patient's anatomical lumen is higher than the pressure in the bottle), water movement will force the moveable flap closed. When the moveable flap closes, it may close against a feature of the sealing body 430. The moveable flap may also close against the end of the water tube 450 or a structural member of the connector assembly. The connector also includes a body that seals around the water inlet tube of the endoscope so that water does not leak to the outside or to the air flow path. It should be noted that some endoscope designs accept water through some other means than a protruding tube (such as a hole to which the connector must mate by means of a gasket); the valve described here would similarly prevent retrograde flow in a design compatible with such an endoscope. In some embodiments, the valve mechanism described here may also be used to prevent retrograde flow of air (or other gasses) through the tube set and endoscope. In embodiments that accept air flow from the endoscope to pressurize the bottle, the valve would only allow air flow from the endoscope to the bottle and would prevent air flow from the bottle to the endoscope. In embodiments that accept air from a separate air source, air would flow from the bottle to the endoscope and the valve would prevent flow in the opposite direction.

Figure 9A:
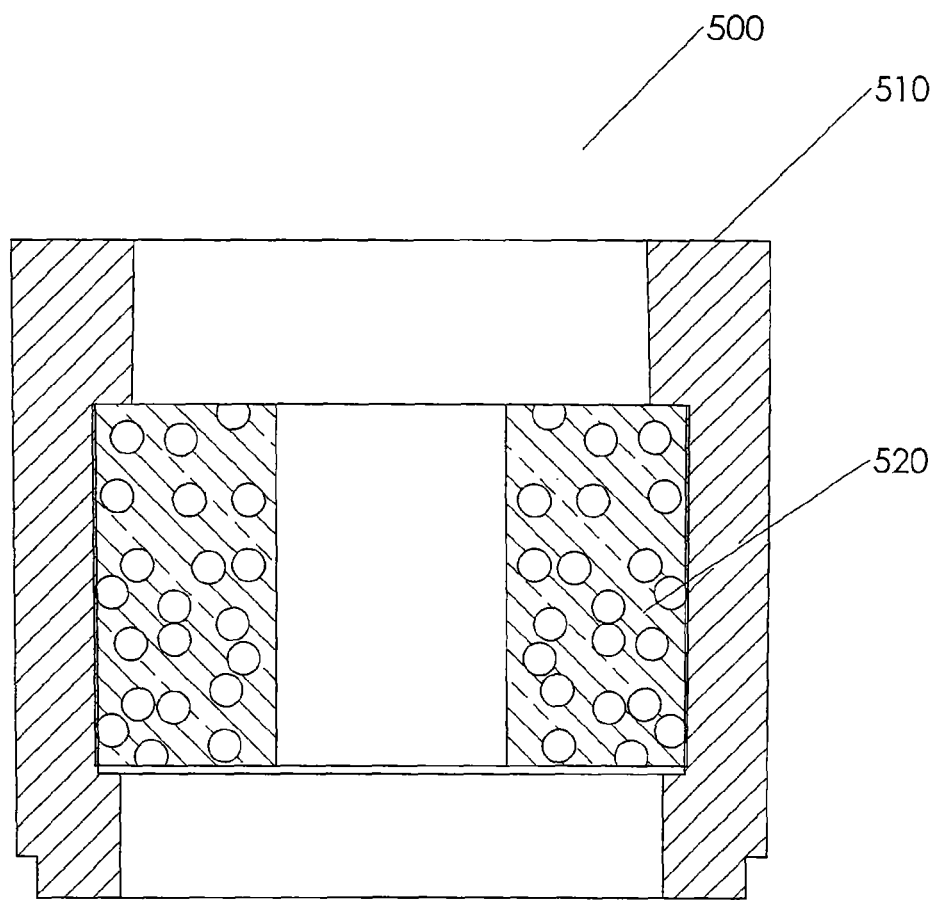
FIG. 9A illustrates an embodiment of an inline air filter assembly.

FIG. 9A is an illustrative embodiment of an inline air filter assembly 500. From a biological safety perspective, the air that enters the water bottle may be filtered via porous medium 520. Air that enters the water bottle without being filtered may carry infectious microorganisms. The illustrated embodiment is a filter that forms a part of the connector that joins the air and water tubes to the bottle cap. As illustrated, the filter is formed as an annular member that surrounds the water tube and fills the space between the air tube and the water tube. The filter is composed of some porous medium 520. Depending on the structural properties of the filter medium, the filter assembly may include a structural member 510 with surfaces for bonding to the bottle cap and the water tube. The water tube may pass through the center of the filter, as illustrated, or it may pass to the side of the filter. All air passing through the tube is filtered. As illustrated, the filter assembly is located where the air tube joins the bottle cap. In other embodiments, the filter assembly 500 may also be located at the end of the air tube that connects to the air/water connector. In such an embodiment, the filter may be incorporated as a structural member 510 of the air/water connector.

Figure 9B:
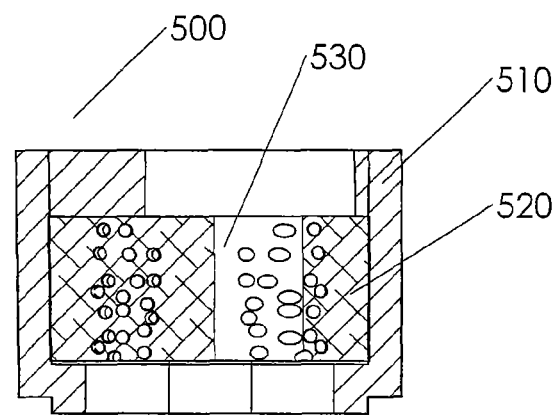
FIG. 9B illustrates an embodiment of an inline air filter assembly with an offset water tube passage.
Figure 9C:
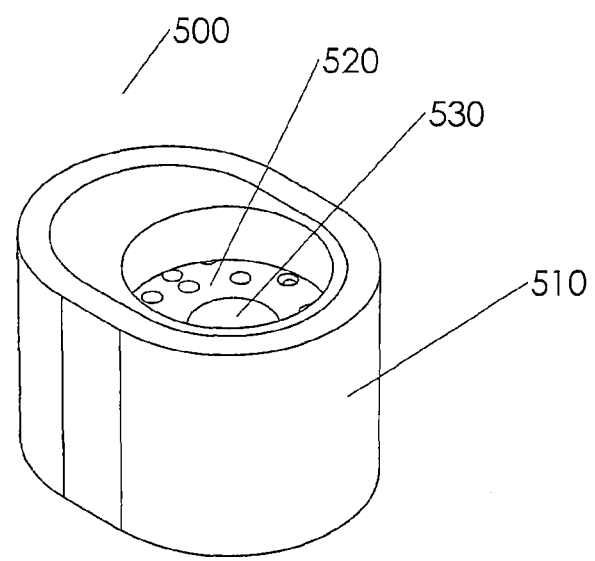
FIG. 9C illustrates an orthogonal view of an embodiment of an inline air filter assembly with an offset water tube passage.

FIG. 9B is an illustrative embodiment of an inline air filter assembly having a porous medium 520 to filter air with an offset water tube passage 530. FIG. 9C illustrates an orthogonal view of an embodiment of an inline air filter assembly 500 with an offset water tube passage 530 configured to receive a water tube. The porous material 520 is configured to filter the air that is fed into the bottle. The air filter assembly comprises structural member 510 that surrounds the filter and allows easy connection to the water tube 530. The porous media can be made of polyethersulfone, PTFE, a PVC, acrylic copolymer, polysulfone, polyvinylidene fluoride, cellulose acetate, cellulose nitrate, mixed esters of cellulose, nylon, polyamide or a combination thereof. The filter can be microporous, and the mean pore size of the media is from about 0.2 micron to about 150 microns. In some embodiments, the filter can have a mean pore size of about 0.22 micron to about 0.8 micron.

Figure 10:
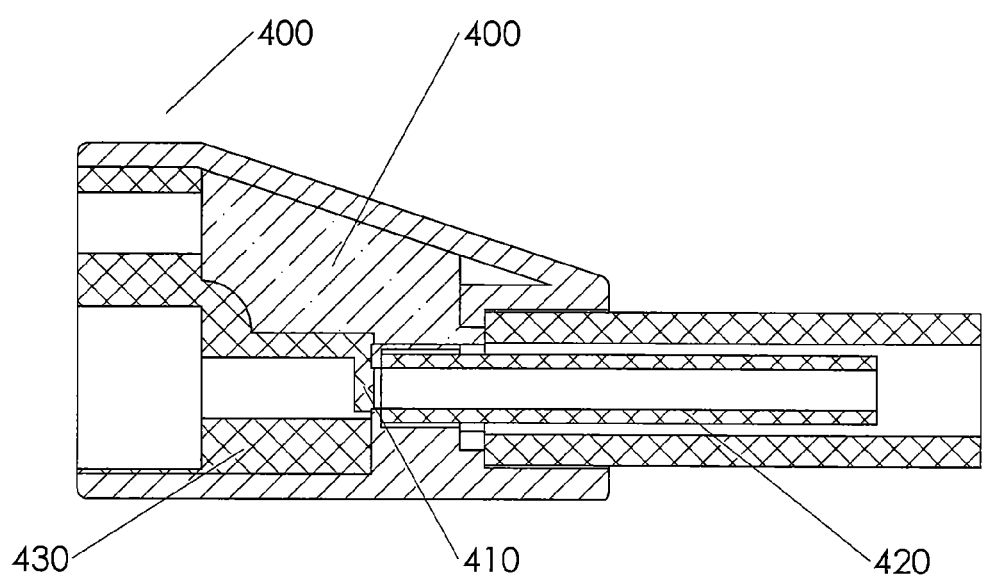
FIG. 10 illustrates an embodiment of an air and water connector with a check valve and an inline air filter.

FIG. 10 is an illustrative embodiment of an air and water connector 400 with a check valve having a movable flap 410 and an inline air filter 440. The illustrated embodiment is a filter that forms a part of the connector that joins the air and water tubes to the bottle cap. The filter is composed of some porous medium. All gas passing through the connector is filtered. The air and water connector includes gasket body 430 for ease of connection to the endoscope.

Figure 11A:
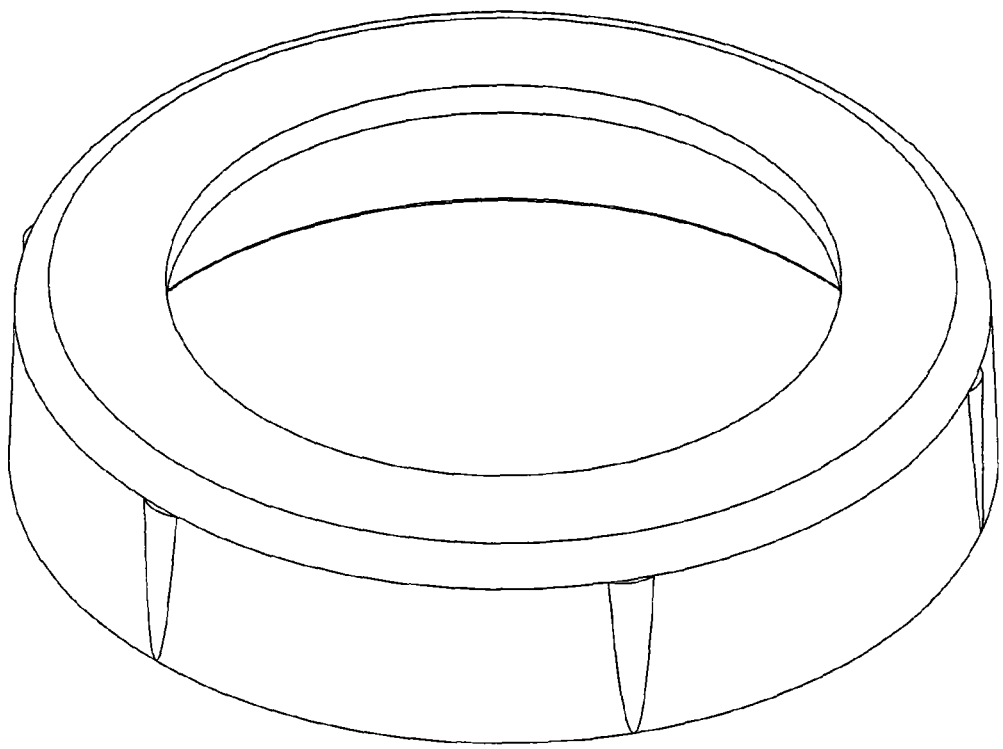
FIG. 11A illustrates an embodiment of a liner.
Figure 11B:
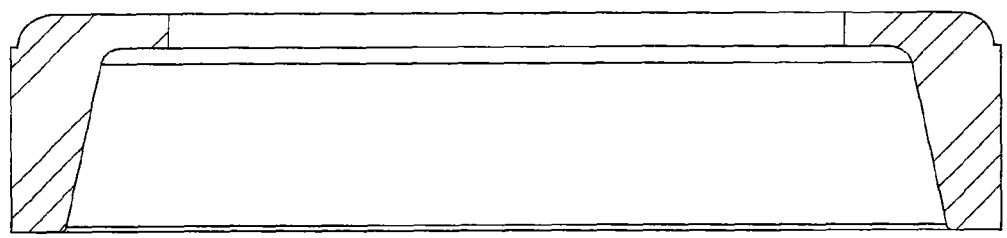
FIG. 11B illustrates a cross sectional view of an embodiment of a liner having a substantially L-shaped cross section.

FIG. 11A illustrates an embodiment of a top view of the liner and FIG. 11B illustrates a cross sectional view of an embodiment of a liner having a substantially L-shaped cross section.

In some embodiments, a cap is provided with a liner inside the cap which is capable of sealing on multiple surfaces, specifically of a variety of bottles including bottles used in medical applications such as endoscopic systems for example. In some embodiments, the cap comprises a thread on an inner surface of said cap and a liner inside the cap which is capable of sealing on multiple surfaces, and a top end wherein the top end comprises at least an opening. The opening can be a hole to fit a tubing. In some embodiments, the cap and the liner are made of the same material including a plastic material, an elastomeric material, thermoplastic elastomeric material, rigid polymer, acrylonitrile butadiene styrene (ABS), methyl methacrylate acrylonitrile butadiene styrene, polyvinyl chloride (PVC), polystyrene, polycarbonate, polypropylene, nylon, silicone, rubber or combination thereof. In some embodiments, the cap and the liner can be one contiguous body. In some embodiments, the liner comprises an inner diameter which is not constant such that it is capable of engaging a variety of bottle necks of varying heights and diameters. In some embodiments, the inner diameter decreases axially toward the top end. In some embodiments, the thread has a first diameter and second diameter, wherein the first diameter is bigger than the second diameter. In some embodiments, the thread is a positive thread.

In some embodiments, a cap is provided comprising a liner capable of sealing on multiple surfaces wherein the cap further comprises on an inner surface a thread, wherein the thread is adapted to engage a variety of bottles. In some embodiments, the thread has a trapezoid geometry comprising a first base and a second base, wherein the first base is larger than the second base and wherein the first base is adjacent to the wall of the cap. In some embodiments, the trapezoidal geometry comprises rounded corners. In some embodiments, the cap and the liner are made of the same material including a plastic material, an elastomeric material, thermoplastic elastomeric material, rigid polymer, acrylonitrile butadiene styrene (ABS), methyl methacrylate acrylonitrile butadiene styrene (MABS), polyvinyl chloride (PVC), polystyrene, polycarbonate, polypropylene, nylon, silicone, rubber or combination thereof. In some embodiments, the cap and the liner can be one contiguous body. In some embodiments, the liner comprises a substantially L-shaped cross section and has varying inner diameters such that it is capable of engaging a variety of bottle necks of varying heights and diameters. Examples of bottles include but are not limited to sterile bottles for medical applications such as sterile water bottles. In some embodiments, the cap comprises an air filter. In some embodiments, the cap comprises a top end and a bottom end, wherein the inner surface is tapered at an angle of about 2 degrees such that the diameter of the bottom end is larger than the diameter of the top end. In some embodiments, a cap is provided comprising at least one gasket such that the gasket provides a seal between the bottle cap and the bottle. In some embodiments, the seal is air tight or nearly air tight.

In some embodiments, the cap comprises a thread on an inner surface, a liner having at least two sealing surfaces at least partially above the thread, and a top end, wherein said top end comprises at least three holes. In some embodiments, at least one of the holes fits an irrigation tubing. In some embodiments, at least one of the holes fits a water/air tube set. In some embodiments, at least one of the holes fits a tubing for insufflation. In some embodiments, a cap is provided that is capable of sealing on multiple surfaces comprising a liner wherein the liner comprises a substantially L-shaped cross sectional profile and having at least two diameters.

In some embodiments, the cap has a thread on an inner surface, wherein the thread is adapted for engaging a variety of bottles and the cap has a top end wherein the top end comprises at least one hole to fit a tubing. In some embodiments, a cap is provided comprising an inner surface having positive threads, wherein the threads are adapted for engaging in a variety of sterile water containers; a top end comprising at least one opening; said opening having a flexible tubing disposed therein. In some embodiments, a liner is provided that is capable of sealing on a variety of caps. In some embodiments, the liner comprises a substantially L-shaped cross-sectional profile comprising various diameters. The liner can be made of thermoplastic elastomer, an elastomeric material, polyvinyl chloride, nylon or combinations thereof.

In some embodiments, a cap is provided comprising a liner capable of sealing on multiple surfaces, wherein the cap comprises at least one hole to fit a tubing and wherein liner seals the area between the cap and the tubing. In some embodiments, a cap is provided for sealing a sterile water bottle comprising a thread on an inner surface providing at least 720° of thread engagement with said sterile water bottle; and at least two sealing surfaces above said thread. In some embodiments, a cap is provided comprising a liner capable of sealing on multiple surfaces; a thread on an inner surface; a top end; wherein the top end comprises at least one hole fit for a tubing wherein the liner seals the area between the cap and the tubing.

Figure 12:
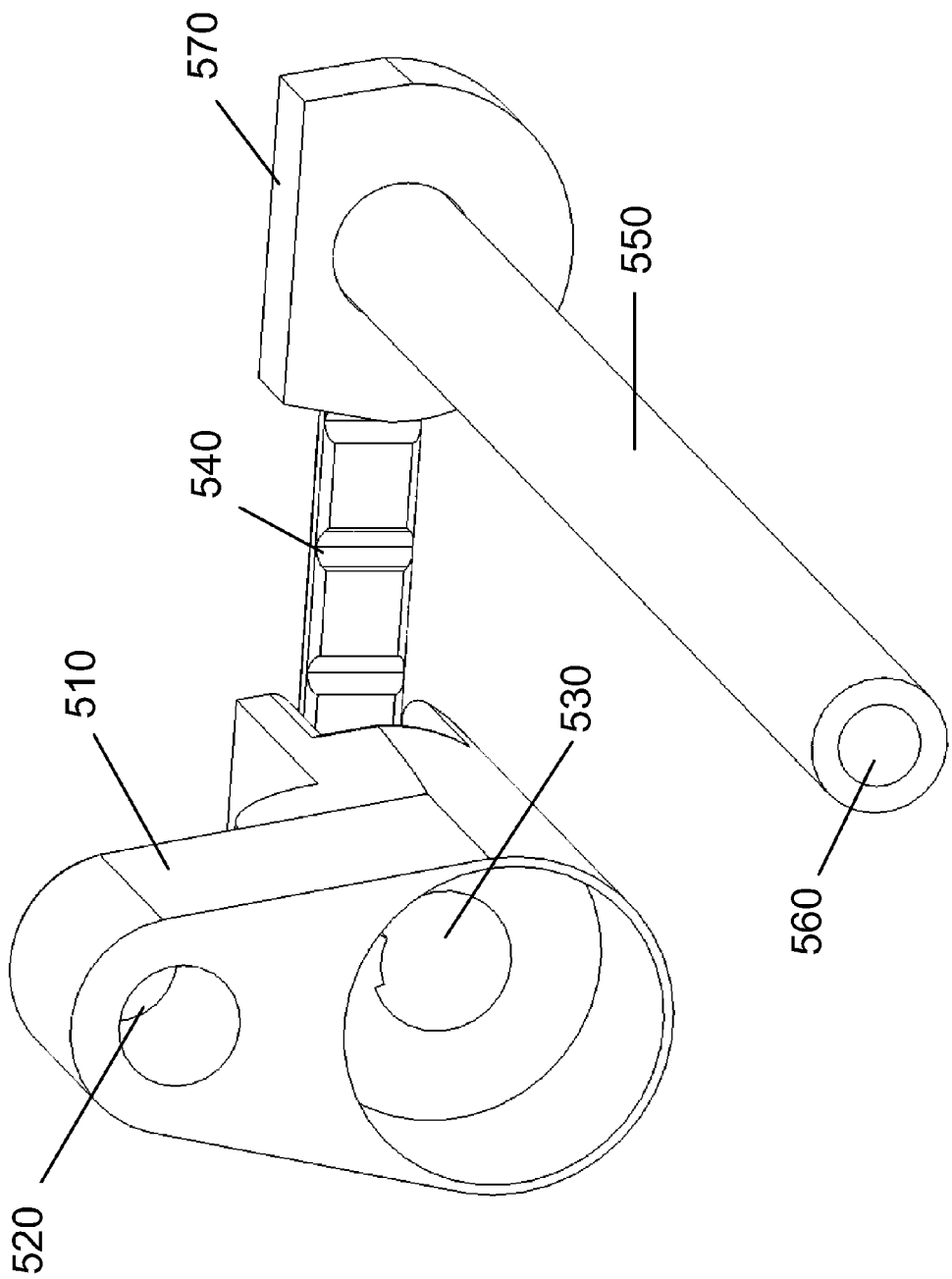
FIG. 12 illustrates a back view of an embodiment of an air and water connector with a back flow valve.

FIG. 12 illustrates a back view of an embodiment of an air and water connector with a back flow valve. In this embodiment, end of water tube 560 can align with moveable flap 530 when hinge 540 is foldably connected to water tube end 570 and moveable flap 530. When the hinge is folded, the moveable flap is pressed into water tube end 570 which then aligns with water tube 550. Moveable flap 530 closes over the end of the water tube to seal the path and prevent water from flowing from the endoscope's water input port to the water tube end 560. A portion of the gasket 510 provides a conduit 520 that is configured to mate with the air port on the endoscope. The gasket 510 can be made from a flexible material such as a thermoplastic elastomer. The moveable flap 530 and the hinge 540 are parts of the gasket. In some embodiments, the air and water connector can be made by overmolding one or more components together.

Figure 13:
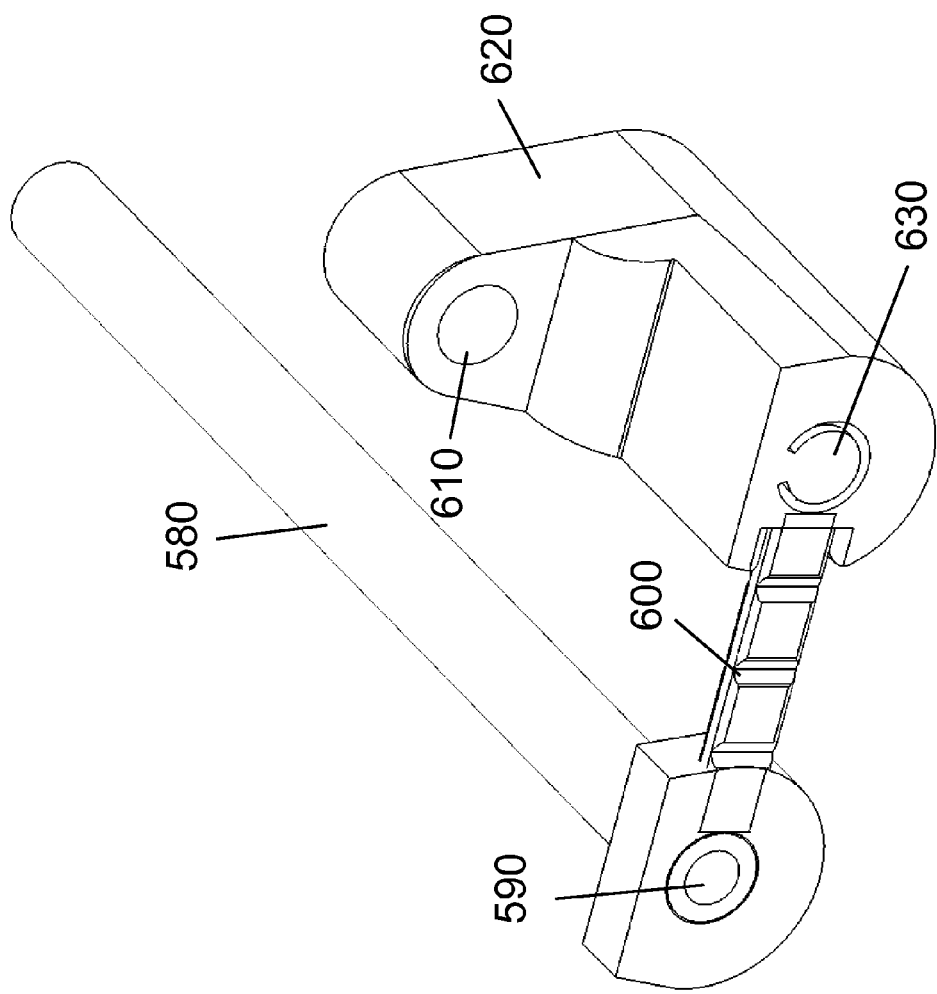
FIG. 13 illustrates a front view of an embodiment of an air and water connector with a back flow valve.

FIG. 13 illustrates a front view of an embodiment of an air and water connector with a back flow valve. In this embodiment, water tube end 590 can align with moveable flap 630 when hinge 600 is foldably connected to water tube end 590 and moveable flap 630. When the hinge is folded, the moveable flap is pressed into water tube end 590 which then aligns with water tube 580. Moveable flap 630 closes over the end of the water tube to seal the path and prevent water from flowing from the endoscope's water input port to the water tube 580. A portion of the gasket 620 provides a conduit 610 that is configured to mate with the air port on the endoscope. The gasket 620 can be made from a flexible material such as a thermoplastic elastomer. The moveable flap 630 and the hinge 600 are parts of the gasket. In some embodiments, the air and water connector can be made by overmolding one or more components together.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A combined tube set comprising: a first tube set utilized to providing rinsing fluid for an endoscope, wherein the first tube set provides an air tube and a water tube, the air tube and the water tube being arranged coaxially at a surface of the bottle cap, the water tube configured to extend through a bottle cap; a second tube set utilized to provide irrigation fluid for the endoscope, wherein the second tube set optionally comprises a flexible section; and a third tube set utilized to provide gas to the system, wherein the second tube set and third tube set is configured to extend through the bottle cap, wherein the bottle cap comprises a liner capable of sealing a surface of a bottle, and a gap is formed between an inner face of the cap and a portion of the liner opposing the inner face, wherein the gap is located between the inner face of the bottle cap and the portion of the liner opposing the inner face, the liner having at least one opening that generally aligns with an opening of the bottle cap, the opening of the liner and the opening of the bottle cap configured to receive the second and the third tube set, and the water tube has a diameter smaller than the air tube, the second tube set and the third tube set.

2. The tube set of claim 1 wherein:
a bottle cap connected to the first tube set and the second tube set, and the third tube set, wherein the bottle cap provides threads that allow the bottle cap to be attached to a variety of different water bottles; and
the liner forms an air-tight seal between the bottle cap and a water bottle.

3. A tube set of claim 2 where the geometry of the liner causes the liner to form an air tight seal on any of several bottles by using a varying inner diameter to compress the liner against the bottles' different outer diameters and/or different rim heights.

4. The tube set of claim 1 further comprising an adaptor or a connector attached to the end of the second tube set, wherein the adaptor or connector is utilized to directly attach the second tube set to the endoscope.

5. A tube set of claim 1, wherein at least one of the tube sets comprise a valve configured to prevent material from moving in a direction of the bottle cap passed the valve.

6. A tube set of claim 1, wherein a distal end of the third tube set is beveled.

7. A tube set of claim 1, wherein the third tube set has a first length defined by a distance between an inner surface of the bottle cap and a tip of the third tube set that is greater than a second length of the water tube defined by a distance between the inner surface of the bottle cap and a tip of the water tube.

8. A tube set of claim 7, wherein the second tube set extends through the bottle cap and has a third length defined by a distance between the inner surface of the bottle cap and a tip of the second tube set that is greater than the first length and the second length.

9. A tube set of claim 1, wherein the air tube is secured to the bottle cap without extending through the bottle cap.

10. A tube set of claim 1, wherein the water tube is discontinuous with the air tube.

11. A tube set of claim 1, wherein the second tube set is configured to extend through the bottle cap.

12. A tube set of claim 1, wherein the third tube set is configured to extend through the bottle cap.

13. A tube set of claim 1, wherein the bottle cap has a reinforced rim attached to the bottle cap to receive the first tube set and the second tube set.

14. A tube set of claim 1, wherein the liner comprises an inclined inner surface configured to engage a variety of bottle necks of varying heights and diameters, and the liner has an inner diameter having a tapered configuration, which is not constant.

15. A tube set of claim 1, wherein the liner has at least one opening configured to receive the first tube set.

16. A tube set of claim 1, wherein the opening of the liner and the opening of the bottle cap are configured to receive the water tube.

17. A tube assembly comprising: a first tube set configured to provide a liquid to an instrument, wherein the first tube set provides a gas and the liquid to the instrument via an air tube and a water tube, the air tube and the water tube being arranged coaxially at a surface of the bottle cap, wherein the water tube extends through a bottle cap and the air tube is secured to the bottle cap without extending through the bottle; and a second tube set configured to provide the liquid to the instrument, wherein the second tube set comprises a flexible section and the second tube set extends through the bottle cap, wherein the bottle cap comprises a liner capable of sealing a surface of a bottle, and a gap is formed between an inner face of the cap and a portion of the liner opposing the inner face of the cap, and the liner having at least one opening that generally aligns with an opening of the bottle cap, the opening of the liner and the opening of the bottle cap configured to receive the second tube set, and the water tube has a diameter smaller than the air tube, and the second tube set.

18. A tube assembly according to claim 17, wherein (i) the tube assembly further comprises a third tube set configured to provide gas to the instrument or (ii) the liquid is the same composition in the first tube set and the second tube set.

19. A tube assembly according to claim 18, wherein at least one of (i) at least a portion of the water tube runs within the air tube and the water tube extends within the bottle; (ii) the air tube is separate from the water tube and the water tube extends within the bottle; or (iii) the first tube set, the second tube set, and the third tube set are separate from each other.

20. A tube assembly according to claim 18, wherein at least one of (i) the first, second, and/or third tube set comprise at least one air filter, pincher clip, back flow valve and/or connector; or (ii) a portion of the first, second, and/or third tube is contained within an adapter.

21. A combined tube set comprising:
- a bottle cap comprising a liner capable of sealing a surface of a bottle, a gap being formed between an inner face of the cap and a portion of the liner opposing the inner face;
- a first tube set utilized to provide rinsing fluid for an endoscope, wherein the first tube set provides an air tube and a water tube, the air tube and the water tube being arranged coaxially at a surface of the bottle cap, the bottle cap having an opening and the liner having an opening aligned with the opening of the bottle cap, and the opening of the bottle cap and the opening of the liner configured to receive the water tube, the water tube extending through the bottle cap;
- a second tube set utilized to provide irrigation fluid for the endoscope, wherein the second tube set optionally comprises a flexible section; and
- a third tube set utilized to provide gas to the system,
- wherein the second tube set and third tube set each extend through the opening of the bottle cap and the opening of the liner, and the water tube has a diameter smaller than the air tube, the second and the third tube set.

22. A combined tube set of claim 21, wherein the first tube set comprises the water tube having a first length below the cap and the second tube set comprises a second length below the cap, and the third tube set comprises a third length below the cap, wherein the first length, the second length and the third length below the cap are all different.

23. A combined tube set of claim 21, wherein the water tube, second and third tube sets are configured to extend through the bottle cap and contact the irrigation and/or rinsing fluid.

\* \* \* \* \*